US012220196B2

(12) United States Patent
Wakana

(10) Patent No.: US 12,220,196 B2
(45) Date of Patent: Feb. 11, 2025

(54) SURGICAL TOOL, SURGERY SUPPORT SYSTEM, AND SURGICAL OPERATING UNIT

(71) Applicant: SONY GROUP CORPORATION, Tokyo (JP)

(72) Inventor: Kazuhito Wakana, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 390 days.

(21) Appl. No.: 17/753,527

(22) PCT Filed: Aug. 24, 2020

(86) PCT No.: PCT/JP2020/031905
§ 371 (c)(1),
(2) Date: Mar. 7, 2022

(87) PCT Pub. No.: WO2021/049286
PCT Pub. Date: Mar. 18, 2021

(65) Prior Publication Data
US 2022/0331036 A1    Oct. 20, 2022

(30) Foreign Application Priority Data
Sep. 13, 2019    (JP) ................. 2019-166763

(51) Int. Cl.
*A61B 34/00*    (2016.01)
*A61B 17/29*    (2006.01)
(Continued)

(52) U.S. Cl.
CPC .............. *A61B 34/71* (2016.02); *A61B 17/29* (2013.01); *A61B 34/37* (2016.02); *B25J 17/02* (2013.01);
(Continued)

(58) Field of Classification Search
CPC ......... A61B 34/71; A61B 34/37; A61B 17/29; A61B 2017/2938; A61B 2034/305; A61B 2034/715; B25J 17/02
See application file for complete search history.

(56) References Cited

U.S. PATENT DOCUMENTS

| 2012/0123217 A1 | 5/2012 | Ramans et al. |
| 2015/0157410 A1 | 6/2015 | Kilroy et al. |

(Continued)

FOREIGN PATENT DOCUMENTS

| CN | 105163679 A | 12/2015 |
| CN | 105813581 A | 7/2016 |

(Continued)

OTHER PUBLICATIONS

International Search Report and Written Opinion of PCT Application No. PCT/JP2020/031905, issued on Nov. 2, 2020, 10 pages of ISRWO.

*Primary Examiner* — Brooke Labranche
(74) *Attorney, Agent, or Firm* — CHIP LAW GROUP

(57) ABSTRACT

A surgical tool having an open-close end effector is to be provided. The surgical tool includes a shaft, a wrist that is connected to the end of the shaft and is rotatable about a first axis, a first jaw member and a second jaw member that are supported rotatably about a second axis with respect to the wrist, sets of first and second forward and backward cables that transmit forces for turning the first jaw member and the second jaw member, respectively, about the second axis, and a turning motion unit that generates a turning motion of the wrist about the first axis so that pre-tension of the set of first forward and backward cables and the set of second forward and backward cables does not change.

10 Claims, 31 Drawing Sheets

(51) Int. Cl.
   *A61B 34/37*   (2016.01)
   *B25J 17/02*   (2006.01)
   *A61B 34/30*   (2016.01)

(52) U.S. Cl.
   CPC . *A61B 2017/2938* (2013.01); *A61B 2034/305* (2016.02); *A61B 2034/715* (2016.02)

(56) References Cited

U.S. PATENT DOCUMENTS

| | | | | |
|---|---|---|---|---|
| 2016/0135914 | A1* | 5/2016 | Isoda | A61B 34/71 606/130 |
| 2016/0310156 | A1 | 10/2016 | Kapadia | |
| 2016/0360949 | A1 | 12/2016 | Hyodo et al. | |

FOREIGN PATENT DOCUMENTS

| | | |
|---|---|---|
| CN | 106061356 A | 10/2016 |
| EP | 1131004 A | 9/2001 |
| EP | 3079610 A1 | 10/2016 |
| EP | 3111821 A1 | 1/2017 |
| EP | 3626179 A1 | 3/2020 |
| JP | 2002-503976 A | 2/2002 |
| JP | 2010-220786 A | 10/2010 |
| JP | 201220786 A * | 10/2010 |
| JP | 2016-518160 A | 6/2016 |
| JP | 2018-534100 A | 11/2018 |
| JP | 2019-501699 A | 1/2019 |
| JP | 2019-034002 A | 3/2019 |
| WO | 2000/030548 A1 | 6/2000 |
| WO | 2014/151621 A1 | 9/2014 |
| WO | 2015/088660 A1 | 6/2015 |
| WO | 2015/129437 A1 | 9/2015 |
| WO | 2019/039612 A2 | 2/2019 |

* cited by examiner

ψ : 0°
θ : 0°
α : 15°

ψ : 0°
θ : 80°
α : 15°

ψ : 0°
θ : 80°
α : 0°

ψ : 0°
θ : -80°
α : 15°

Ψ : -80°
θ : 80°
α : 15°

Ψ : 80°
θ : 80°
α : 15°

Ψ : -45°
θ : -45°
α : 0°

Ψ : 80°
θ : -80°
α : 0°

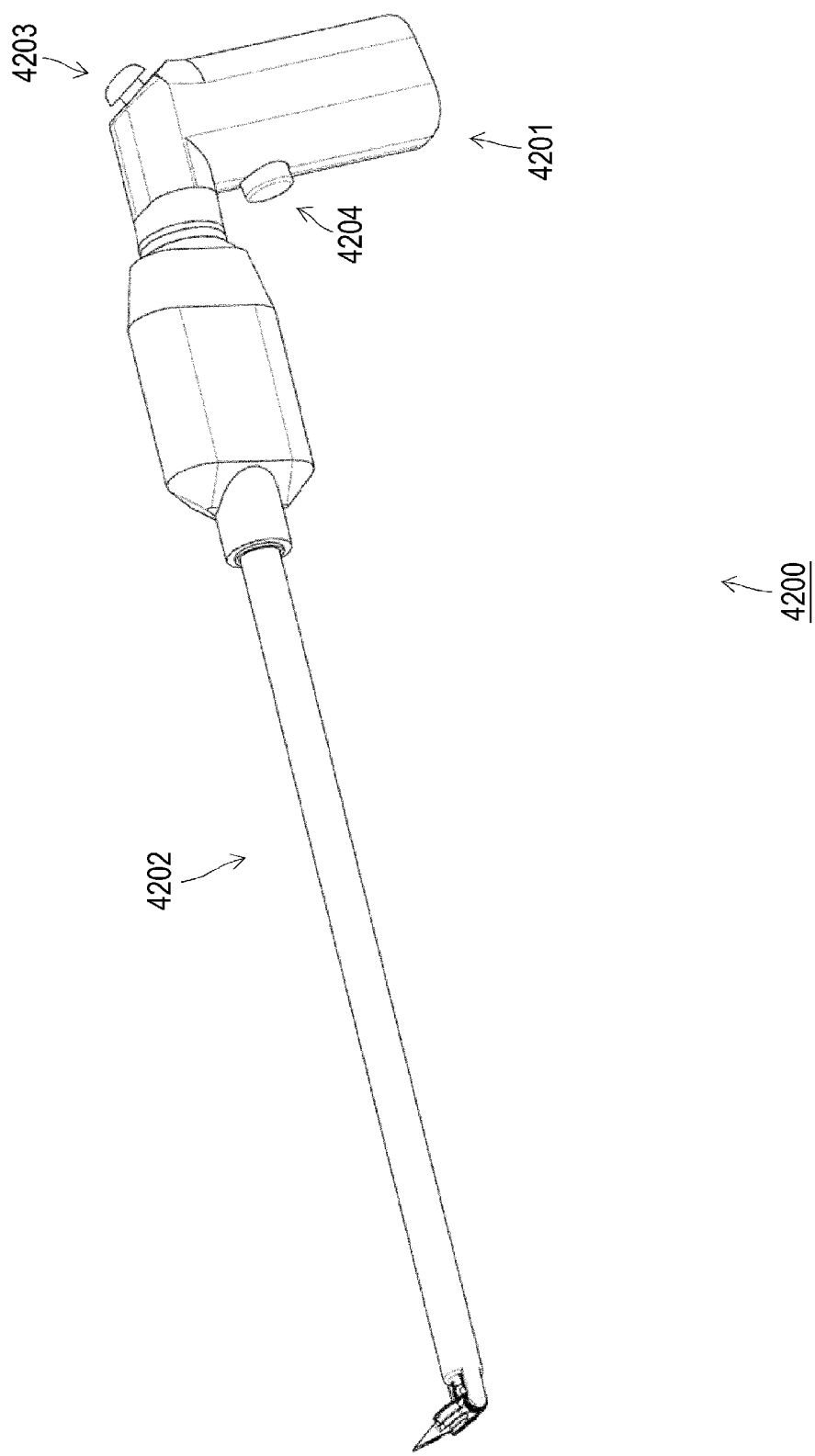

SURGICAL TOOL, SURGERY SUPPORT SYSTEM, AND SURGICAL OPERATING UNIT

CROSS REFERENCE TO RELATED APPLICATIONS

This application is a U.S. National Phase of International Patent Application No. PCT/JP2020/031905 filed on Aug. 24, 2020, which claims priority benefit of Japanese Patent Application No. JP 2019-166763 filed in the Japan Patent Office on Sep. 13, 2019. Each of the above-referenced applications is herebyincorporated herein by reference in its entirety.

TECHNICAL FIELD

The technology disclosed in this specification (hereinafter referred to as "the present disclosure") relates to a surgical tool to be used in a surgical robot, for example, a surgery support system, and a surgical operating unit.

BACKGROUND ART

Advances in the robotics technologies in recent years are remarkable, and robots are now widely used in work sites in various industrial fields. For example, in the field medicine, a master-slave surgical robot is becoming widespread. This kind of surgical robot is designed so that an operator such as a surgeon operates, from the master side, one or a plurality of surgical tools included in a slave device. Also, as a known method for controlling a master-slave system, there is a bilateral method by which a slave device is operated from a master device, and at the same time, the state of the slave device is fed back to the master device (see Patent Document 1, for example).

An end effector having an opening and closing mechanism such as forceps is provided at the end of a surgical tool mounted in a slave device. Further, on the assumption that a surgical tool is to be used in an operation in a body cavity, on a body surface, or the like, the end of a surgical tool is strongly desired to have multiple degrees of freedom, have a small diameter, be small in size, and be light in weight. Specifically, the end of a surgical tool is desired to have a total of three degrees of freedom, which are two degrees of freedom of rotation and a degree of freedom of opening and closing. Further, for miniaturization of surgical tools, a drive method using a cable is often adopted in handling the end of a surgical tool (see Patent Documents 2 to 4, for example).

CITATION LIST

Patent Documents

Patent Document 1: Japanese Patent Application Laid-Open No. 2019-34002
Patent Document 2: Japanese Patent Application Laid-Open No. 09-542671
Patent Document 3: JP 2018-534100 W
Patent Document 4: JP 2019-501699 W

SUMMARY OF THE INVENTION

Problems to be Solved by the Invention

An object of the technology according to the present disclosure is to provide a surgical tool that has an open-close end effector such as forceps, is designed to be small in size and light in weight, and is used in a surgery support system, and to provide a surgical robot and a surgical operating unit.

Solutions to Problems

A first aspect of the technology according to the present disclosure is
a surgical tool that includes:
a shaft;
a wrist that is connected to the end of the shaft and is rotatable about a first axis;
a first jaw member and a second jaw member that are supported rotatably about a second axis with respect to the wrist;
a set of first forward and backward cables that transmits a force for turning the first jaw member about the second axis;
a set of second forward and backward cables that transmits a force for turning the second jaw member about the second axis; and
a turning motion unit that generates a turning motion of the wrist about the first axis so that pre-tension of the set of first forward and backward cables and the set of second forward and backward cables does not change.

The turning motion unit generates a turning motion of the wrist about the first axis by causing one of the set of first forward and backward cables and the set of second forward and backward cables to move backward and the other one to move forward in the longitudinal axis direction of the shaft.

Alternatively, the turning motion unit includes: a wrist capstan that is provided on the wrist and has the first axis as its rotation axis, the set of third forward and backward cables being wound around the wrist capstan; and a third actuator that rotates a third drive capstan and pulls the third cable set. The turning motion unit causes a turning motion of the wrist about the first axis while adjusting the pre-tension of the set of first forward and backward cables and the set of second forward and backward cables. However, the first actuator and the first drive capstan, and the second actuator and the second drive capstan are secured to the shaft.

Further, a second aspect of the technology according to the present disclosure is
a surgery support system that includes a surgical tool, and an arm to which the surgical tool is attached,
the surgical tool including:
a shaft;
a wrist that is connected to the end of the shaft and is rotatable about a first axis;
a first jaw member and a second jaw member that are supported rotatably about a second axis with respect to the wrist;
a set of first forward and backward cables that transmits a force for turning the first jaw member about the second axis;
a set of second forward and backward cables that transmits a force for turning the second jaw member about the second axis; and
a turning motion unit that generates a turning motion of the wrist about the first axis so that pre-tension of the set of first forward and backward cables and the set of second forward and backward cables does not change.

Further, a third aspect of the technology according to the present disclosure is
a surgical operating unit that includes a surgical tool, and a handle unit to which the surgical tool is attached, the surgical tool including:

a shaft;

a wrist that is connected to the end of the shaft and is rotatable about a first axis;

a first jaw member and a second jaw member that are supported rotatably about a second axis with respect to the wrist;

a set of first forward and backward cables that transmits a force for turning the first jaw member about the second axis;

a set of second forward and backward cables that transmits a force for turning the second jaw member about the second axis; and a turning motion unit that generates a turning motion of the wrist about the first axis so that pre-tension of the set of first forward and backward cables and the set of second forward and backward cables does not change.

Effects of the Invention

By the technology according to the present disclosure, it is possible to provide a surgical tool that has an open-close end effector such as forceps, includes a smaller number of components, has a smaller diameter, and is used in a surgical robot, and to provide a surgery support system and a surgical operating unit.

Note that the advantageous effects described in this specification are merely examples, and the advantageous effects to be brought about by the technology according to the present disclosure are not limited to them. Furthermore, in some cases, the technology according to the present disclosure may exhibit additional advantageous effects, in addition to the above advantageous effects.

Other objects, features, and advantages of the technology according to the present disclosure will be made apparent by the embodiments described below and the detailed descriptions with reference to the accompanying drawings.

BRIEF DESCRIPTION OF DRAWINGS

FIG. 42 is a diagram showing an example external configuration of a surgical operating unit 4200.

MODE FOR CARRYING OUT THE INVENTION

Figure 1:
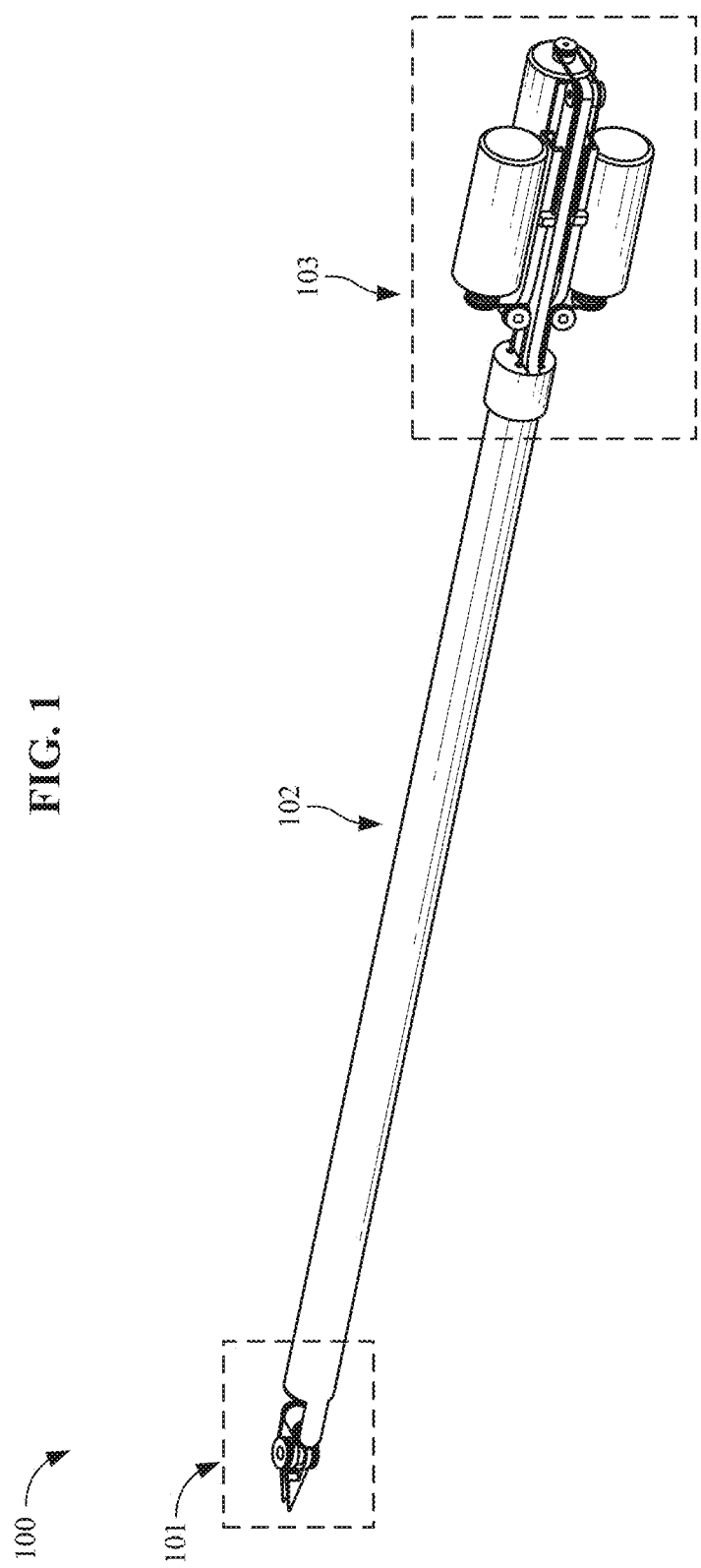
FIG. 1 is a diagram showing an example configuration of a surgical tool unit 100.

In the description below, the technology according to the present disclosure will be explained in the following order, with reference to the drawings.

A. Problems with a Surgical Tool Unit

B. Example Configuration (1) of a Surgical Tool Unit (with reference to FIGS. 1 to 22)

C. Example Configuration (2) of a Surgical Tool Unit (with reference to FIGS. 23 to 30)

D. Example Configuration (3) of a Surgical Tool Unit (with reference to FIGS. 31 to 40)

E. Modifications of the Surgical Tool Unit

F. Example Applications of the Surgical Tool Unit (with reference to FIGS. 41 and 42)

G. Effects

A. Problems with a Surgical Tool Unit

A surgical tool to be used in a surgical robot preferably has a total of three degrees of freedom, which are two degrees of freedom of rotation and a degree of freedom of opening and closing at the end. Specifically, such a surgical tool includes an open-close end effector formed with a pair of opposing jaw members, a wrist supporting the end effector, and a shaft that has a longitudinal axis and connects the wrist to its end, for example. This kind of surgical tool has a degree-of-freedom configuration including: a first axis for turning the wrist about the yaw axis, for example, with respect to the end of the shaft; a second axis for turning the orientation of the end effector about the pitch axis, for example, with respect to the wrist; and a third axis (an open-close shaft) for opening and closing the jaw members. In the description below, an embodiment in which the second axis and the open-close shaft are coaxial will be described.

In laparoscopic surgery, for example, the end (distal end) side of the shaft is normally used while inserted in a body cavity via a trocar, and therefore, needs to have a small diameter. Further, in brain surgery, treatment needs to be performed on a narrow operative field, and therefore, it is necessary to minimize hindering of the field of view of the operator, depending on the surgical tool. In view of this, the driving forces generated by actuators (electromagnetic rotary motors, for example) disposed on the root side (the proximal end) of the shaft are basically transmitted via cables, so as to operate the surgical tool. Specifically, three systems of cables for transmitting the power for turning the wrist about the first axis with respect to the shaft end, the power for turning the monitoring orientation about the second axis with respect to the wrist, and the power for opening and closing the open-close end effector are required, and these cables are inserted through the shaft. Further, in a power transmission mechanism using cables, a plurality of pulleys is used, such as capstans for applying power to the cables or converting the forces from the cables into axial forces, and idler pulleys to be used for adjusting the layout of the cables in the shaft and applying constant tension to the cables.

Here, according to a method by which the layout of cables is adjusted with idler pulleys, high slidability is achieved. Thus, excellent durability and reliability are also achieved, and torque control on the end effector can be performed with high precision. On the other hand, the number of components increases by the number of idler pulleys. Therefore, the surgical tool (or the outer diameter of the shaft, for example) becomes larger in size, and the costs become higher. According to a method by which the cables are made to slide on an R surface formed on a peripheral component without the use of any idler pulley, it is possible to reduce the number of components and achieve a smaller size by eliminating the idler pulleys. However, the cables easily deteriorate due to abrasion, and the reliability becomes poorer. Furthermore, the friction coefficient on the sliding surface is high, which leads to disturbance. As a result, torque control becomes difficult. It is also possible to adopt a method by which cables are inserted through a round hole formed along a desired layout. However, backlash occurs when the cables inserted through the round hole are handled.

Also, a cable loop type or an individual cable traction type can be normally adopted as a method for driving a capstan on the output side with a cable tractive force generated by an actuator.

In the former cable loop type, the cables are laid out by looping the output-side capstan and the drive-side capstan that is rotated by drive of an actuator. With the cable loop type, the forward and backward cables can be controlled in an antagonistic manner by a single actuator, it is easy to make the drive unit smaller in size and lighter in weight. Furthermore, there is no need to compensate the pre-tension of the cables with an output of the actuator, and thus, the actuator can be easily made smaller in size. However, in the case of a device configuration in which the entire length of the looped cables fluctuates due to the influence of the axis angle of the control target and other axes, the pre-tension to be applied to the cables fluctuates, and therefore, it is difficult to adopt the cable loop type. For example, when the wrist is driven to rotate about the first axis, the lengths of the respective cable for driving the respective jaw members change.

On the other hand, the latter individual cable traction type has a configuration in which the forward and backward cables attached to the capstans on the output side are pulled by individual actuators, and the forward and backward cables can be controlled independently of each other. Thus, the degree of freedom in designing the configuration of a surgical tool becomes higher. However, the pre-tension of the cables needs to be compensated with outputs of the actuators. Although it is also possible to compensate the pre-tension using a coil spring, a weight, or the like, control becomes difficult because the corresponding spring force or inertial force is applied when driving is performed with the actuators.

In both the cable loop type and the individual cable traction type, one traction motor is required for each one cable. If heavy and large motors for compensating the pre-tension of the cables are installed as many as the number of cables, the housing space and the device weight increase. Also, in both the cable loop type and the individual cable traction type, a total of two cables that are forward and backward cables are used for bidirectionally rotating one output-side capstan. Therefore, two idler pulleys for adjusting the layout of the cables are also required, and the number of components increases.

Furthermore, a yaw operation, a pitch operation, and an opening and closing operation of the end effector at the end of a surgical tool need to be performed with a structure that does not cause cross-axis interference. Cross-axis interference will lead to the following events, for example.

(1) When the yaw axis angle is changed, the pitch axis passively rotates.

(2) When the yaw axis angle is changed, the pre-tension of the cables fluctuates.

In view of the above, this specification discloses below a surgical tool that achieves size and weight reduction by adjusting the layout of cables with a smaller number of idler pulleys, and pulling the cables by a method that facilitates application of desired pre-tension. This specification also discloses below a computer-aided surgery system and a surgical operating unit.

B. Example Configuration (1) of a Surgical Tool Unit

FIG. 1 shows an example configuration of a surgical tool unit to which the technology according to the present disclosure is applied. A surgical tool unit 100 shown in the drawing includes a hollow shaft 102 having a longitudinal axis, a surgical tool unit end portion 101 at one end of the shaft 102, and a surgical tool unit drive unit 103 at the other end of the shaft 102. The surgical tool unit end portion 101 includes a wrist element capable of turning about a first axis parallel to the yaw axis with respect to the shaft 102, and an end effector at the end of the wrist element. The end effector performs an opening and closing operation with a second axis functioning as the open-close shaft, the second axis being parallel to the pitch axis. The end effector is formed with a pair of opposing jaw members that turn about the second axis and perform an opening and closing operation. However, the second axis is located at a position offset from the first axis. Meanwhile, the surgical tool unit drive unit 103 includes two actuators that drive the respective jaw members in the surgical tool unit end portion 101, and one actuator that drives the wrist.

Figure 2:
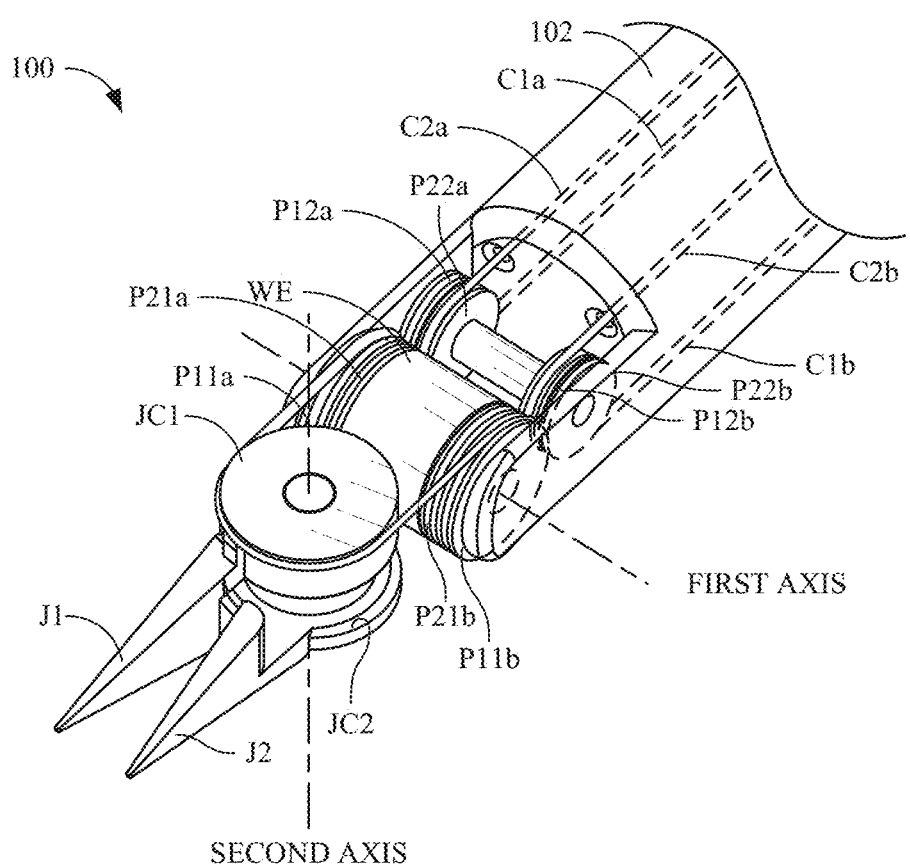
FIG. 2 is an enlarged view of a surgical tool unit end portion 101.
Figure 3:
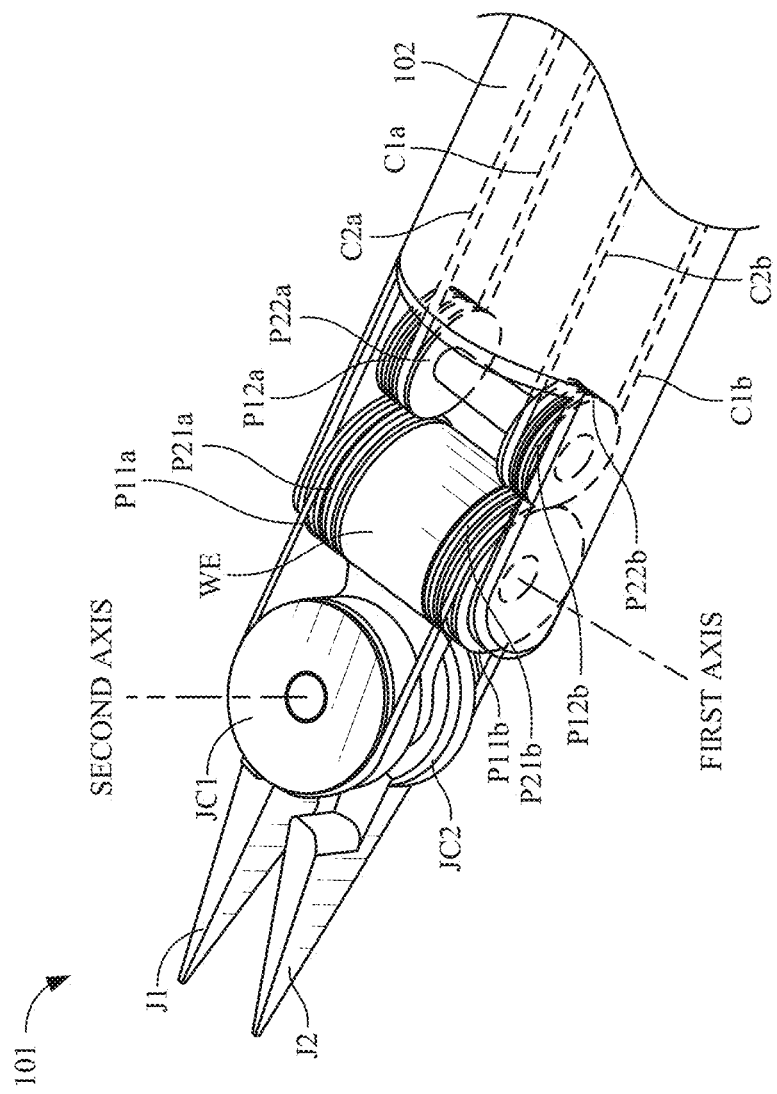
FIG. 3 is an enlarged view of the surgical tool unit end portion 101.
Figure 4:
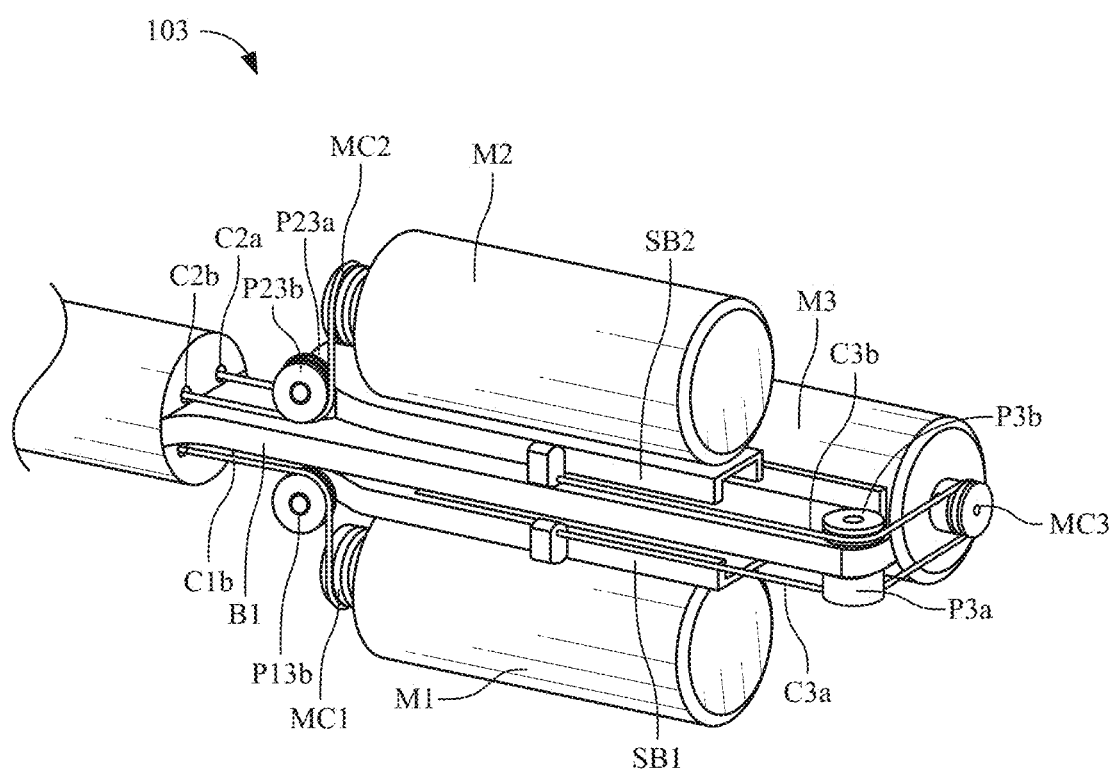
FIG. 4 is an enlarged view of a surgical tool unit drive unit 103.
Figure 5:
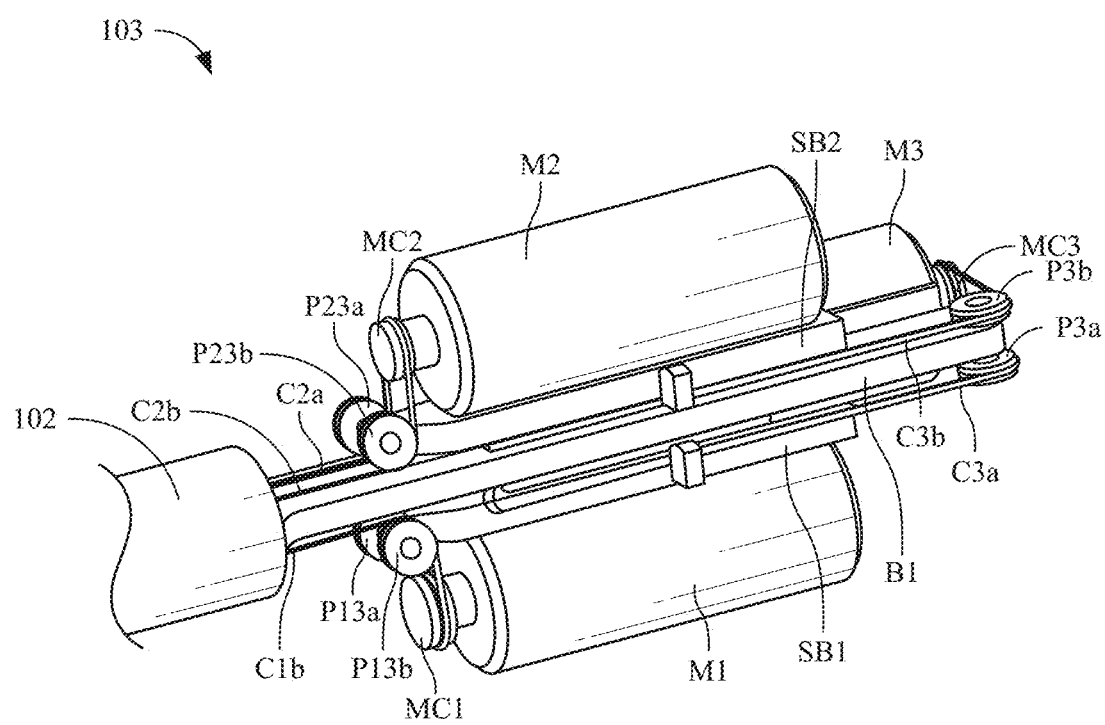
FIG. 5 is an enlarged view of the surgical tool unit drive unit 103.
Figure 6:
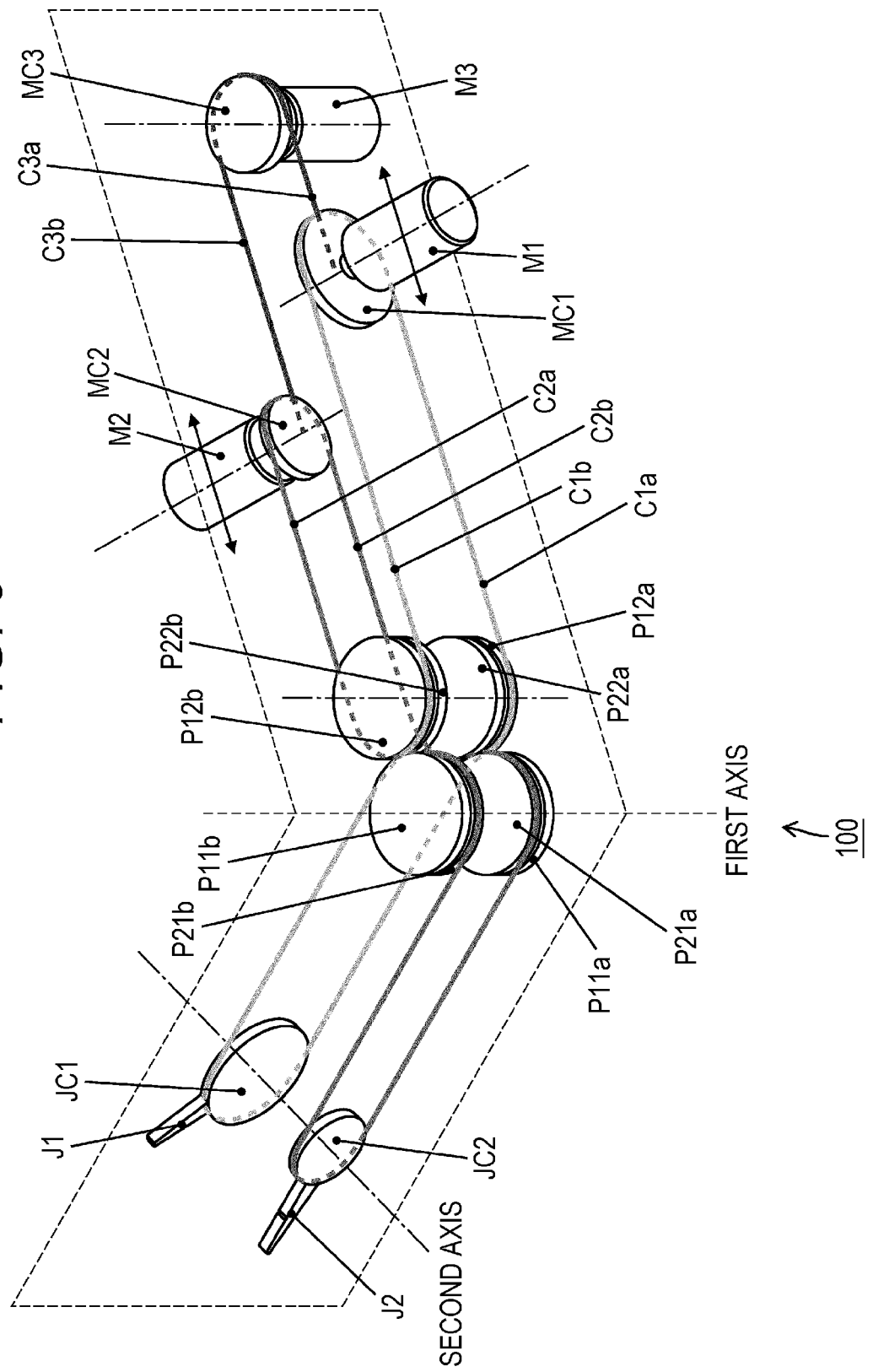
FIG. 6 is a diagram showing an example degree-of-freedom configuration of the surgical tool unit 100.
Figure 7:
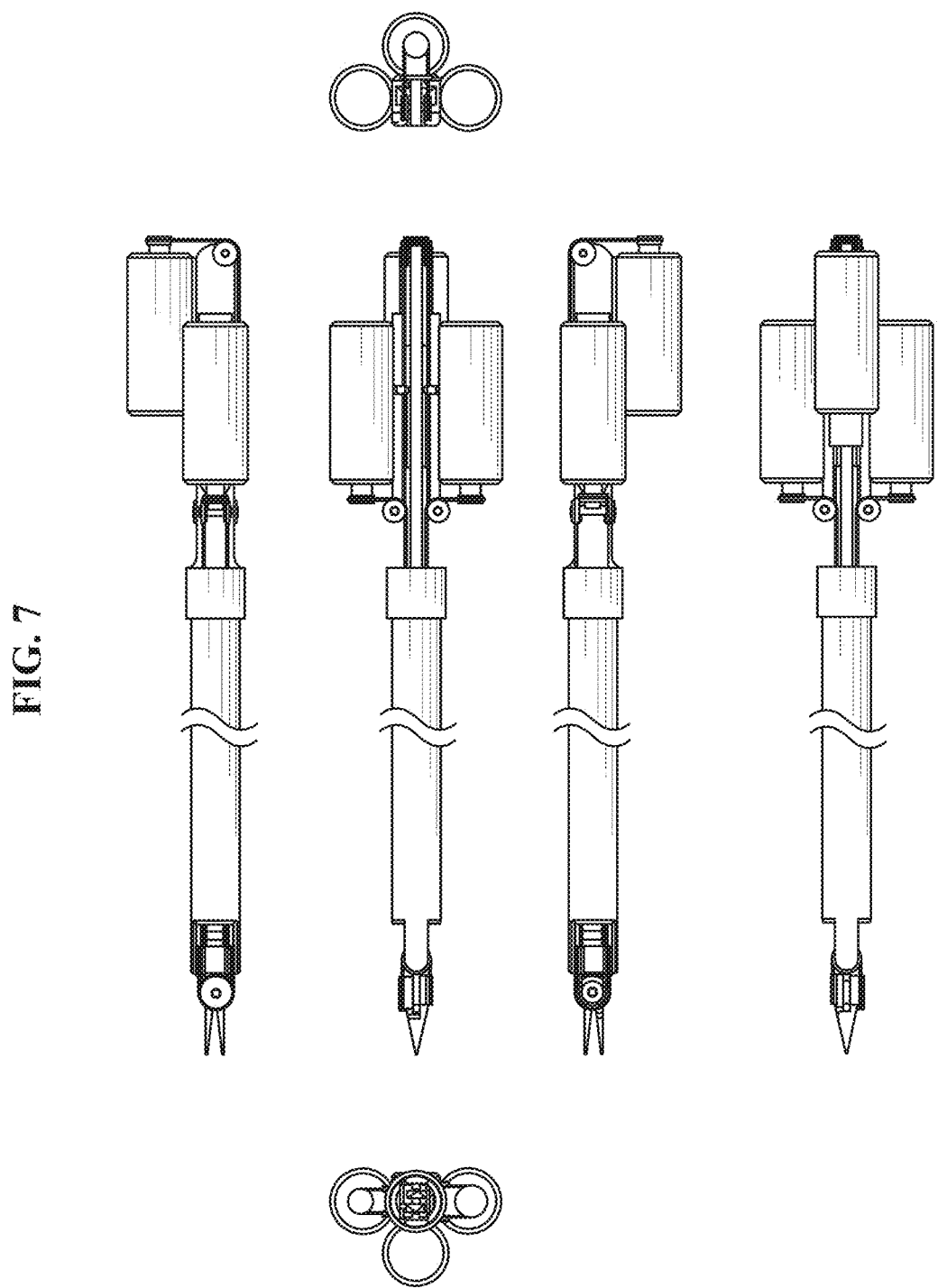
FIG. 7 is a diagram showing a six-sided view of the surgical tool unit 100.
Figure 8:
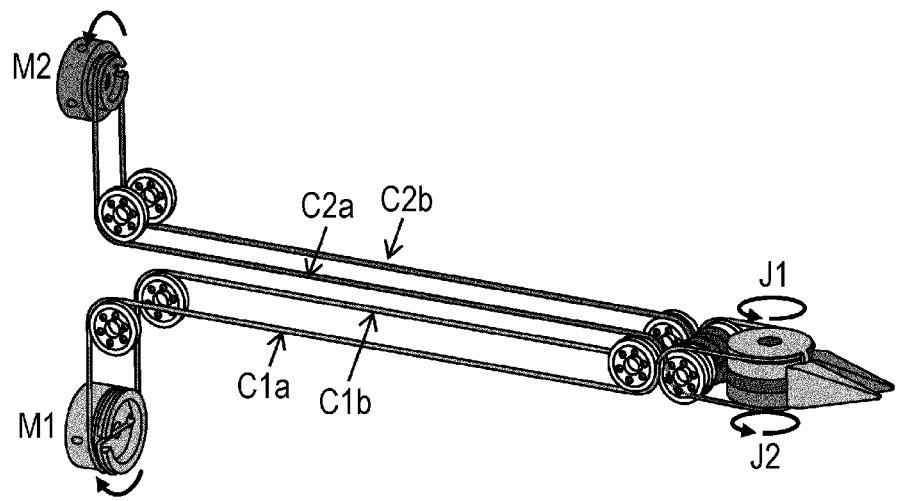
FIG. 8 is a diagram showing a simplified example degree-of-freedom configuration of the surgical tool unit 100.
Figure 9:
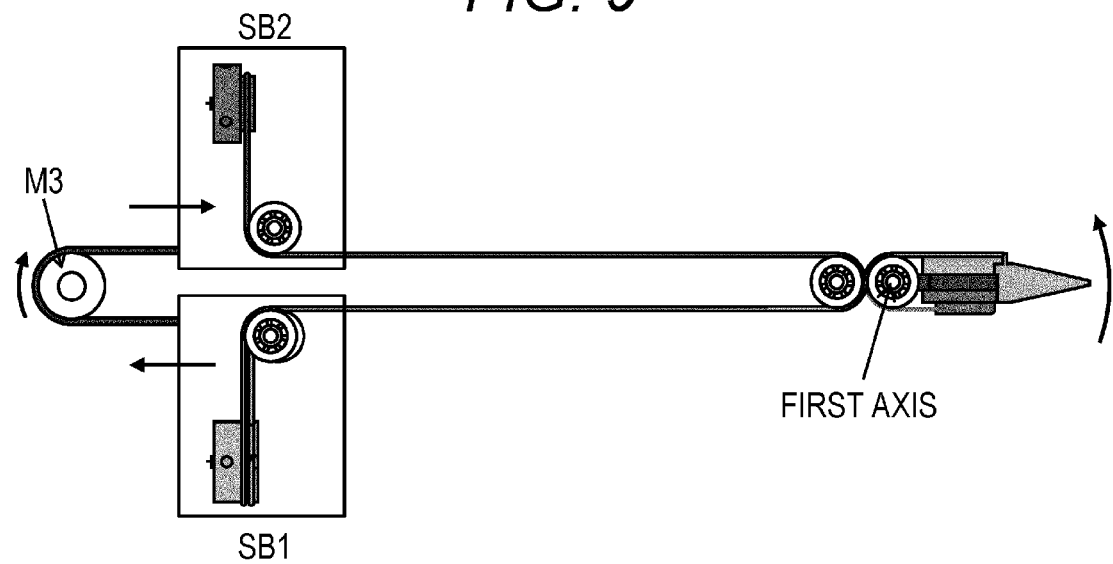
FIG. 9 is a diagram showing a simplified example degree-of-freedom configuration of the surgical tool unit 100.

FIGS. 2 and 3 show the surgical tool unit end portion 101 in an enlarged manner (however, the viewing direction is different between FIGS. 2 and 3). Also, FIGS. 4 and 5 show the surgical tool unit drive unit 103 in an enlarged manner (however, the viewing direction is different between FIGS. 4 and 5). Further, FIG. 6 shows an example degree-of-freedom configuration of the surgical tool unit 100. Furthermore, FIG. 7 shows a six-sided view of the surgical tool unit 100. Further, FIGS. 8 and 9 show a simplified configuration relating to the degree of freedom of the surgical tool unit 100.

The surgical tool unit end portion 101 includes a wrist element WE and an open-close end effector. The end effector includes a pair of opposing jaw members: a first jaw member J1 and a second jaw member J2 (see FIGS. 2 and 3, for example). The wrist element WE is supported at a portion near the root so as to be able to turn about the first axis parallel to the yaw axis at the end (distal end) of the shaft 102. Further, the first jaw member J1 and the second jaw member J2 that constitute the end effector are supported so as to be able to turn about the second axis parallel to the pitch axis at the end of the wrist element WE. The first jaw member J1 and the second jaw member J2 open and close when the open angle with the second axis serving as the open-close shaft changes.

Meanwhile, the surgical tool unit drive unit 103 includes a first motor M1 to be used for driving the first jaw member J1, a second motor M2 to be used for driving the second jaw member J2, and a third motor M3 to be used for driving the wrist element WE (see FIGS. 4, 5, and 6, for example). Further, first to third motor capstans MC1, MC2, and MC3 as drive capstans are attached to the output shafts of the first to third motors M1 to M3, respectively (see FIG. 6, for example). Although a rotary motor is assumed to be used for each of the first to third motors M1 to M3, a motor with a speed reducer may also be used.

A set of first forward and backward cables C1a and C1b is wound around the first motor capstan MC1, and the first motor capstan MC1 is rotated by the first motor M1, so that the first jaw member J1 is driven by a cable loop method. Also, a set of second forward and backward cables C2a and C2b is wound around the second motor capstan MC2, and the second motor capstan MC2 is rotated by the second motor M2, so that the second jaw member J2 is driven by the cable loop method.

Referring to FIGS. 4 and 5, the first motor M1 is supported on a first slide base SB1 that slides in the longitudinal axis direction of the shaft 102, and the second motor M2 is supported on a second slide base SB2 that slides in the longitudinal axis direction of the shaft 102. Further, a set of third forward and backward cables C3a and C3b is wound around the third motor capstan MC3 via third idler pulleys P3a and P3b. The other end of the third forward cable C3a is secured to the first slide base SB1, and the other end of the third backward cable C3b is secured to the second slide base SB2. The third motor M3 then pulls the set of third forward and backward cables C3a and C3b by the cable loop method, so that the first slide base SB1 and the second slide base SB2 can be moved forward and backward in opposite directions in the longitudinal axis direction of the shaft 102 (see FIG. 6, for example).

Referring to FIGS. 2 and 3, the first jaw member J1 is supported by the wrist element WE at a portion near the base, so as to be able to turn about the second axis. Likewise, the second jaw member J2 is supported by the wrist element WE at a portion near the base, so as to be able to turn about the second axis. Accordingly, each of the first jaw member J1 and the second jaw member J2 is turned about the second axis, so that the open angle of the first jaw member J1 and the second jaw member J2 become larger or smaller (in other words, so that a change is caused in the difference between the angles of the first jaw member J1 and the second jaw member J2 about the second axis). Thus, an opening and closing operation of the end effector is performed. Further, the first jaw member J1 and the second jaw member J2 are simultaneously turned about the second axis, while the open angle of the first jaw member J1 and the second jaw member J2 are maintained at constant angles (in other words, to cause a change in the sum of the angles of the first jaw member J1 and the second jaw member J2 about the second axis). Thus, a turning operation of the end effector formed with the first jaw member J1 and the second jaw member J2 about the second axis is performed.

Referring to FIGS. 2, 3, and 6, a first jaw capstan JC1 having the above-mentioned second axis as its rotation axis is provided near the root of the first jaw member J1. The set of first forward and backward cables C1a and C1b is wound around the first jaw capstan JC1. As shown in FIGS. 4 to 6, the set of first forward and backward cables C1a and C1b is wound around the first motor capstan MC1 on the side of the surgical tool unit drive unit 103. Accordingly, a tractive force acts on one of the cables C1a and C1b depending on the rotation direction of the first motor M1, and a turning operation of the first jaw member J1 about the second axis is performed. As the first jaw member J1 is driven by the cable loop method using the set of first forward and backward cables C1a and C1b, it is possible to make the range of movement of the first jaw member J1 wider.

Also, referring to FIGS. 2, 3, and 6, a second jaw capstan JC2 having the above-mentioned second axis as its rotation axis is provided near the root of the second jaw member J2. The set of second forward and backward cables C2a and C2b is wound around the second jaw capstan JC2. As shown in FIGS. 4 to 6, the set of second forward and backward cables C2a and C2b is wound around the second motor capstan MC2 on the side of the surgical tool unit drive unit 103. Accordingly, a tractive force acts on one of the cables C2a and C2b depending on the rotation direction of the second motor M2, and a turning operation of the second jaw member J2 about the second axis is performed. As the second jaw member J2 is driven by the cable loop method using the set of second forward and backward cables C2a and C2b, it is possible to make the range of movement of the second jaw member J2 wider.

Next, the layout of the respective cables in the surgical tool unit 100, and a specific method for operating the surgical tool unit end portion 101 are described.

Idler pulleys are used to redirect each cable of the set of first forward and backward cables C1a and C1b and the set of second forward and backward cables C2a and C2b at a portion near the first axis so that each of the cables is inserted through the shaft 102, and to adjust the layout of the respective cables in the shaft 102.

As shown in FIGS. 2, 3, and 6, the first forward cable C1a is pulled in a direction orthogonal to the second axis. However, the direction of the cable C1a is switched to a direction orthogonal to the first axis by a first idler pulley P11a that uses the first axis as its rotation axis, and further, the layout is adjusted so that the first forward cable C1a is inserted through the shaft 102 by a first adjacent idler pulley P12a that is adjacent to the first idler pulley P11a and has a rotation axis parallel to the first axis. After inserted through the shaft 102, the first forward cable C1a is then wound around the first motor capstan MC1 via an idler pulley P13a as shown in FIG. 5.

Meanwhile, the first backward cable C1b is pulled in a direction orthogonal to the second axis. However, the direction of the cable C1b is switched to a direction orthogonal to the first axis by a first idler pulley P11b that uses the first axis as its rotation axis, and further, the layout is adjusted so that the first backward cable C1b is inserted through the shaft 102 by a first adjacent idler pulley P12b that is adjacent to the first idler pulley P11b and has a rotation axis parallel to the first axis. After inserted through the shaft 102, the first backward cable C1b is then wound around the first motor capstan MC1 via an idler pulley P13b from the opposite direction to the first forward cable C1a, as shown in FIG. 5.

In short, the set of first forward and backward cables C1a and C1b is laid out so as to perform power transmission between the first jaw capstan JC1 and the first motor capstan MC1 by the cable loop method. Accordingly, as can also be seen from FIG. 8, the first motor capstan MC1 is rotated by the first motor M1, so that the rotation of the first jaw capstan JC1 can adjust the turning angle of the first jaw member J1 about the second axis.

Also, as shown in FIGS. 2, 3, and 6, the second forward cable C2a is pulled in a direction orthogonal to the second axis. However, the direction of the cable C2a is switched to a direction orthogonal to the first axis by a second idler pulley P21a that uses the first axis as its rotation axis, and further, the layout is adjusted so that the second forward cable C2a is inserted through the shaft 102 by a second adjacent idler pulley P22a that is adjacent to the second idler pulley P21a and has a rotation axis parallel to the first axis. After inserted through the shaft 102, the second forward cable C2a is then wound around the second motor capstan MC2 via an idler pulley P23a as shown in FIG. 5.

Meanwhile, the second backward cable C2b is pulled in a direction orthogonal to the second axis. However, the direction of the cable C2b is switched to a direction orthogonal to the first axis by a second idler pulley P21b that uses the first axis as its rotation axis, and further, the layout is adjusted so that the second backward cable C2b is inserted through the shaft 102 by a second adjacent idler pulley P22b that is adjacent to the second idler pulley P21b and has a rotation axis parallel to the first axis. After inserted through the shaft 102, the first backward cable C1b is then wound around the second motor capstan MC2 via an idler pulley P23b from the opposite direction to the second forward cable C2a, as shown in FIG. 5.

In short, the set of second forward and backward cables C2a and C2b is laid out so as to perform power transmission between the second jaw capstan JC2 and the second motor capstan MC2 by the cable loop method. Accordingly, as can also be seen from FIG. 8, the second motor capstan MC2 is rotated by the second motor M2, so that the rotation of the second jaw capstan JC2 can adjust the turning angle of the second jaw member J2 about the second axis.

The tractive force of the set of first forward and backward cables C1a and C1b and the set of second forward and backward cables C2a and C2b is controlled by the first motor M1 and the second motor M2 so that a change is caused in the difference between the angles of the first jaw member J1 and the second jaw member J2 about the second axis. Thus, an opening and closing operation of the end effector formed with the pair of jaw members J1 and J2 can be performed. The open-close angle is determined by the difference between the angles of the first jaw member J1 and the second jaw member J2 about the second axis.

Also, the tractive force of the set of first forward and backward cables C1a and C1b and the set of second forward and backward cables C2a and C2b is controlled by the first motor M1 and the second motor M2 so that a change is caused in the sum of the angles of the first jaw member J1 and the second jaw member J2 about the second axis. Thus, the end effector can be made to turn about the second axis. The average value of the angles of the first jaw member J1 and the second jaw member J2 about the second axis is the turning angle of the end effector about the second axis.

Meanwhile, the first motor M1, together with the first motor capstan MC1 and each of the idler pulleys P13a and P13b, is secured to the first slide base SB1. Also, the second motor M2, together with the second motor capstan MC2 and each of the idler pulleys P23a and P23b, is secured to the first slide base SB1. Further, the third forward cable C3a is joined to the first slide base SB1 via the idler pulley P3a. Also, the third backward cable C3b is joined to the second slide base SB2 via the third idler pulley P3b.

Note that the third forward cable C3a in the section from the first slide base SB1 to the third idler pulley P3a, and the third backward cable C3b in the section from the second slide base SB2 to the third idler pulley P3b are preferably laid out so as to be parallel to the longitudinal axis of the shaft 102.

In short, the set of third forward and backward cables C3a and C3b is laid out so as to perform power transmission between the third motor capstan MC3, and the first and second slide bases SB1 and SB2. Accordingly, as can be seen from FIG. 9, when the third motor capstan MC3 is rotated by the third motor M3, the first slide base SB1 and the second slide base SB2 can be moved forward and backward in opposite directions in the longitudinal axis direction of the shaft 102.

Referring to FIGS. 6 and 8, the set of second forward and backward cables C2a and C2b is wound around the second idler pulleys P21a and P21b, from the opposite direction to the direction in which the set of first forward and backward cables C1a and C1a is wound around the first idler pulleys P11a and P11b. Therefore, when the set of first forward and backward cables C1a and C1a is moved backward and when the set of second forward and backward cables C2a and C2a is moved backward, rotative forces in opposite directions about the first axis are applied to the wrist element WE. Accordingly, when the first slide base SB1 is moved forward to the end (which is the distal end) of the shaft 102, and the second slide base SB2 is moved backward to the root side (which is the proximal end) of the shaft 102, the set of first forward and backward cables C1a and C1a moves forward, and the set of second forward and backward cables C2a and C2b moves backward. As a result, the wrist element WE rotates in the positive direction about the first axis. Conversely, when the first slide base SB1 is moved backward, and the second slide base SB2 is moved forward, the set of first forward and backward cables C1a and C1a moves backward, and the set of second forward and backward cables C2a and C2b moves forward. As a result, the wrist element WE rotates in the negative direction about the first axis. Here, it is assumed that both the set of first forward and backward cables C1a and C1b and the set of second forward and backward cables C2a and C2b have a constant total length.

Figure 10:
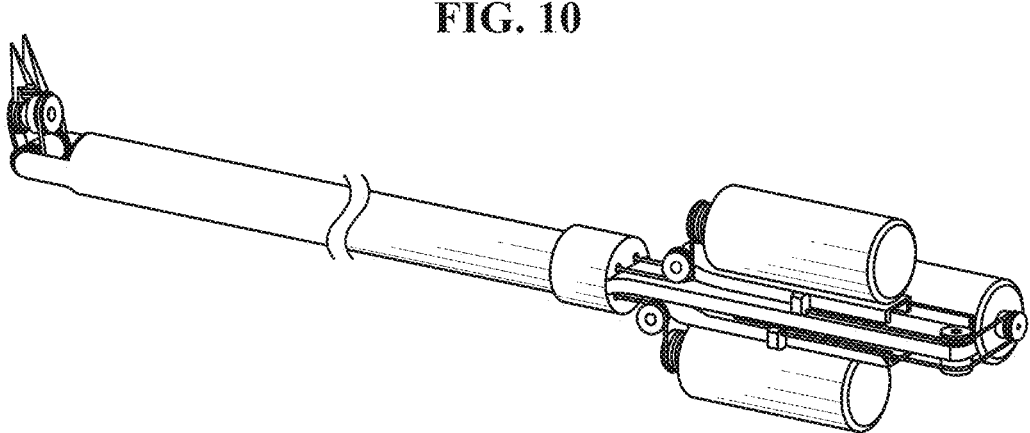
FIG. 10 is a diagram showing a state in which a wrist element WE is turned about the first axis.
Figure 11:
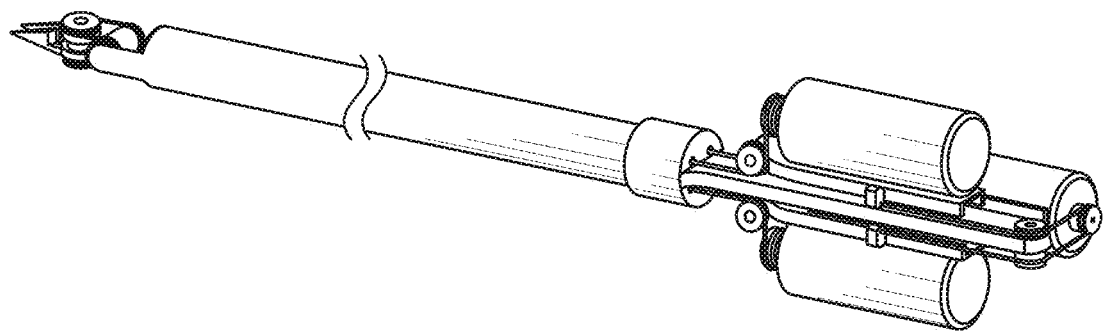
FIG. 11 is a diagram showing a state in which the wrist element WE is turned about the first axis.
Figure 12:
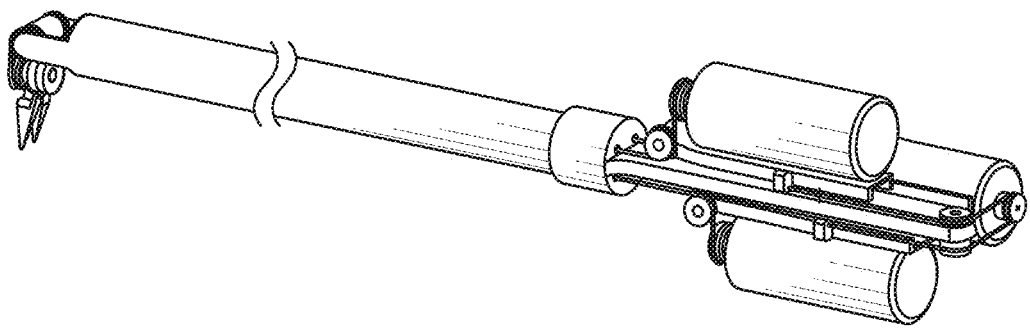
FIG. 12 is a diagram showing a state in which the wrist element WE is turned about the first axis.

FIGS. 10 to 12 each show a state in which the wrist element WE is turned about the first axis by drive of the third motor M3. As can be seen from FIGS. 10 to 12, by the drive of the third motor M3, the first slide base SB1 on which the first motor M1 is mounted, and the second slide base SB2 on which the second motor M2 is mounted move forward and backward in the longitudinal axis direction of the shaft 102.

By rotational drive of the third motor M3, the second slide base SB2 is pulled with the backward cable C3b, and is moved backward to the proximal end side in the longitudinal axis direction of the shaft 102. The wrist element WE is then pulled by the set of second forward and backward cables C2a and C2b, and rotates 80 degrees about the first axis as shown in FIG. 10.

Further, in a case where the positions of the first slide base SB1 and the second slide base SB2 in the longitudinal axis direction of the shaft 102 are the same, the rotational position of the wrist element WE about the first axis is 0 degrees, as shown in FIG. 11.

Also, by rotational drive of the third motor M3 in the opposite direction, the first slide base SB1 is pulled with the forward cable C3a, and is moved backward to the proximal end side in the longitudinal axis direction of the shaft 102. The wrist element WE is then pulled by the set of first forward and backward cables C1a and C1b, and rotates −80 degrees about the first axis as shown in FIG. 12.

In this manner, the third motor M3 pulls the set of third forward and backward cables C3a and C3b, and the set of first forward and backward cables C1a and C1b and the set of second forward and backward cables C2a and C2b are moved forward and backward through sliding operations of the first slide base SB1 and the second slide base SB2. Thus, the wrist element WE can be turned about the first axis. Furthermore, when the wrist element WE is turned about the first axis, the pre-tension of the set of first forward and backward cables C1a and C1b and the set of second forward and backward cables C2a and C2b does not change.

The operation methods in the surgical tool unit end portion 101 are summarized below.

Operation at the First Axis:

When the third motor capstan MC3 is rotated by the third motor M3, a tractive force is generated in one cable of the set of third forward and backward cables C3a and C3b. As a result, as shown in FIGS. 10 to 12, the wrist element WE and the end effector mounted on the wrist element WE can be rotated in the positive direction or the reverse direction about the first axis.

Operation at the Second Axis:

The average value of the angle of the first jaw member J1 about the second axis and the angle of the second jaw member J2 about the second axis is defined as the angle of the end effector about the second axis. When the first jaw capstan JC1 and the second jaw capstan JC2 are rotated in the same direction and at the same speed, a turning operation of the end effector about the second axis is caused.

Operation of the End Effector:

The end effector is formed with a pair of opposing jaw members: the first jaw member J1 and the second jaw member J2 (see FIG. 2, for example). The open angle of the first jaw member J1 and the second jaw member J2 is set as the open-close angle of the end effector. When the first motor capstan MC1 and the second motor capstan MC2 are rotated in opposite directions at the same speed, an opening and closing operation of the end effector is caused.

Next, the relationship between operations of the first to third motors M1 to M3 and operations of the surgical tool unit end portion 101 is described.

Figure 13:
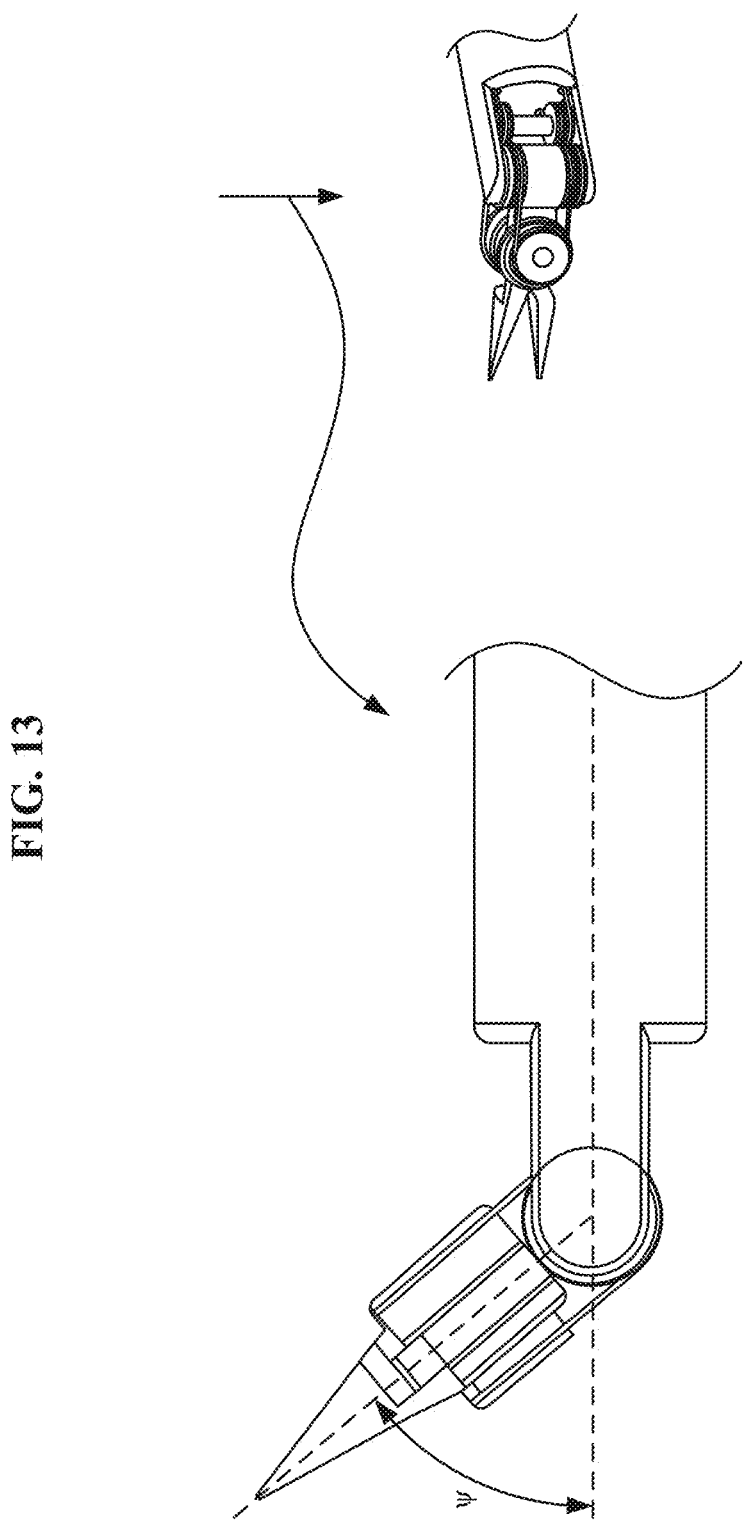
FIG. 13 is a diagram showing an example operation of the wrist element WE turning about the first axis.

FIG. 13 shows an example operation of the wrist element WE about the first axis. Here, the drawing is a view of the surgical tool unit end portion 101 as viewed from a direction parallel to the first axis. As shown in the drawing, the radius of each of the idler pulleys P11a, P11b, P21a, and P21b that rotate about the first axis is represented by $R_\psi$, and the turning angle of the wrist element WE about the first axis is $\psi$.

Figure 14:
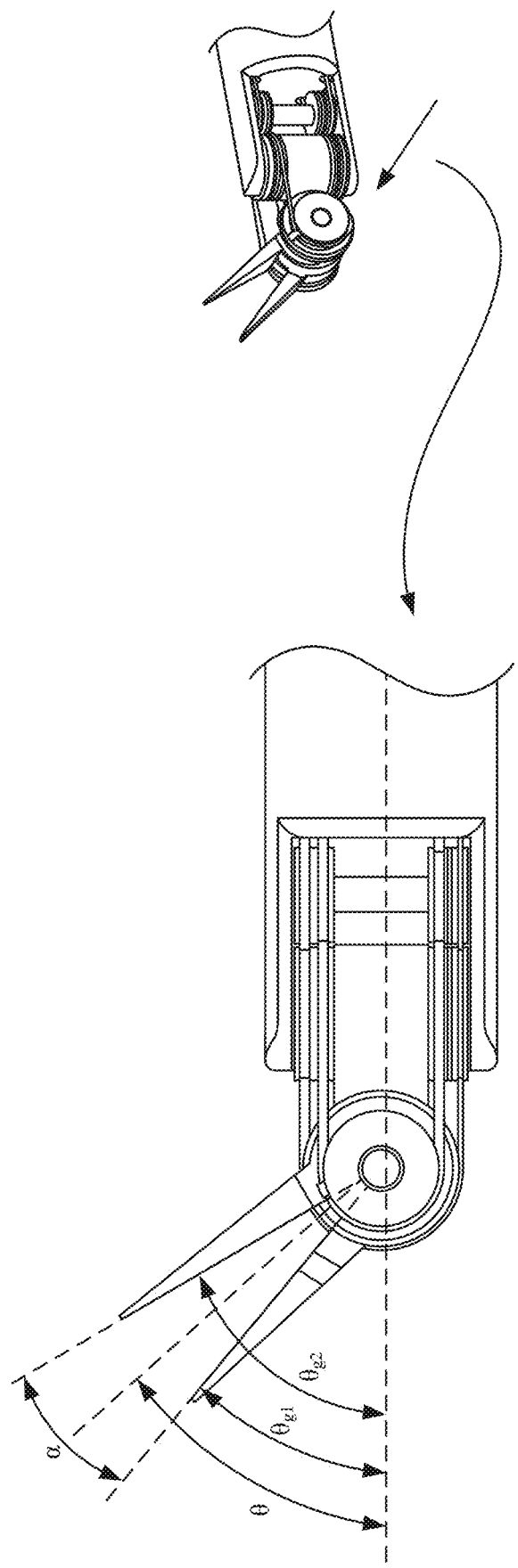
FIG. 14 is a diagram showing an example operation of an end effector turning about the second axis.

Further, FIG. 14 shows an example operation of the end effector about the second axis. Here, the drawing is a view of the surgical tool unit end portion 101 as viewed from a direction parallel to the second axis. As shown in the drawing, the pulley radius of the first jaw capstan JC1 is represented by $R_{JC1}$, the pulley radius of the second jaw capstan JC2 is $R_{JC2}$, the turning angle of the first jaw member J1 about the second axis is $\theta_{j1}$, the turning angle of the second jaw member J2 about the second axis is $\theta_{j2}$, the open angle of the end effector is $\alpha$, and the turning angle of the end effector about the second axis is $\theta$.

Further, although not shown in the drawing, the pulley radius of the first motor capstan MC1 is represented by $R_{MC1}$, the pulley radius of the second motor capstan MC2 is $R_{MC2}$, the pulley radius of the third motor capstan MC3 is $R_{MC3}$, the rotation angle of the first motor capstan MC1 is $\sigma_{MC1}$, the rotation angle of the second motor capstan MC2 is $\sigma_{MC2}$, and the rotation angle of the third motor capstan MC3 is $\sigma_{MC3}$.

Here, the turning angle $\psi$ of the wrist element WE about the first axis, the turning angle $\theta$ of the end effector about the second axis, and the open angle $\alpha$ of the end effector are expressed as in the following Equations (1) to (3), respectively.

[Mathematical Formula 1]
$$\psi = \frac{R_{MC3}}{R_\psi} \phi_{MC3} \tag{1}$$

[Mathematical Formula 2]
$$\theta = \frac{\theta_{j1} + \theta_{j2}}{2} \tag{2}$$

[Mathematical Formula 3]
$$\alpha = \theta_{j1} - \theta_{j2} \tag{3}$$

Meanwhile, the turning angle $\theta_{j1}$ of the first jaw member J1 about the second axis, and the turning angle $\theta_{j2}$ of the second jaw member J2 about the second axis are expressed as in the following Equations (4) and (5), respectively.

[Mathematical Formula 4]
$$\theta_{j1} = \frac{R_{MC1}}{R_{JC1}} \phi_{MC1} \tag{4}$$

-continued

[Mathematical Formula 5]

$$\theta_{j2} = \frac{R_{MC2}}{R_{JC2}} \phi_{MC2} \quad (5)$$

As can be seen from the above Equations (1) to (5), the turning angle ψ of the wrist element WE about the first axis, the turning angle θ of the end effector about the second axis, and the open angle α of the end effector can be independently driven without affecting one another. Thus, the surgical tool unit 100 has a structure that does not cause cross-axis interference.

Next, the range of movement of the surgical tool unit end portion 101 is described.

FIGS. 15 to 22 show examples of turning operations of the wrist element WE about the first axis, turning operations of the end effector about the second axis, and opening and closing operations of the end effector.

Figure 15:
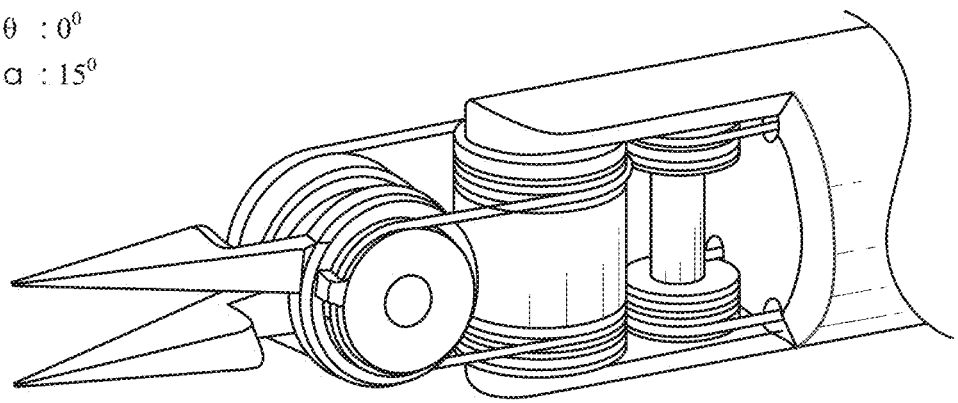
FIG. 15 is a diagram showing an example operation of the surgical tool unit end portion 101.
Figure 16:
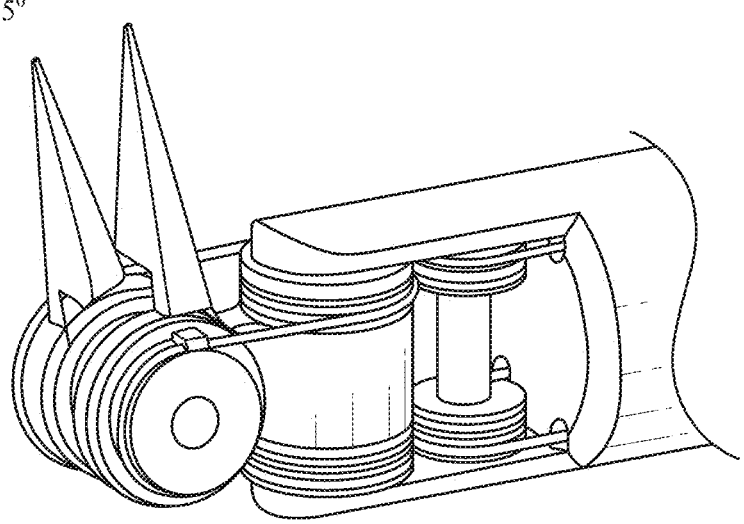
FIG. 16 is a diagram showing an example operation of the surgical tool unit end portion 101.
Figure 17:
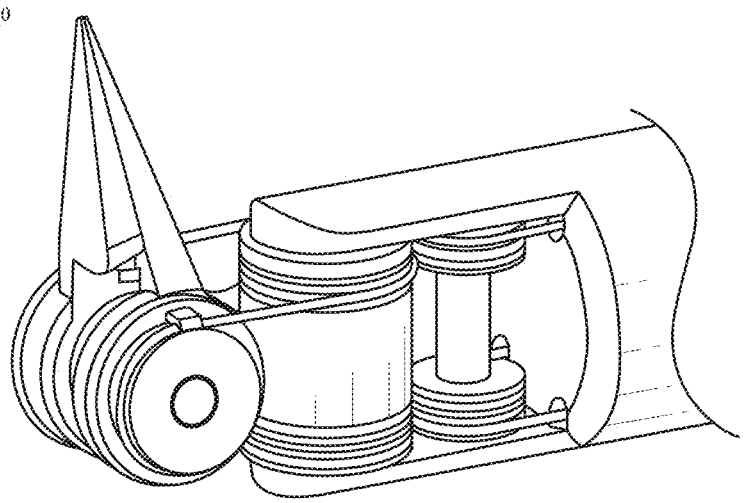
FIG. 17 is a diagram showing an example operation of the surgical tool unit end portion 101.
Figure 18:
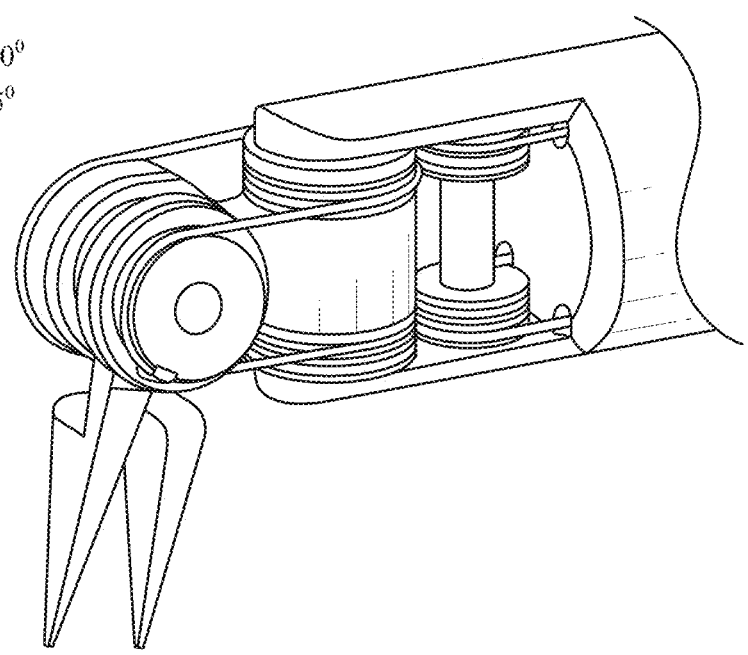
FIG. 18 is a diagram showing an example operation of the surgical tool unit end portion 101.
Figure 19:
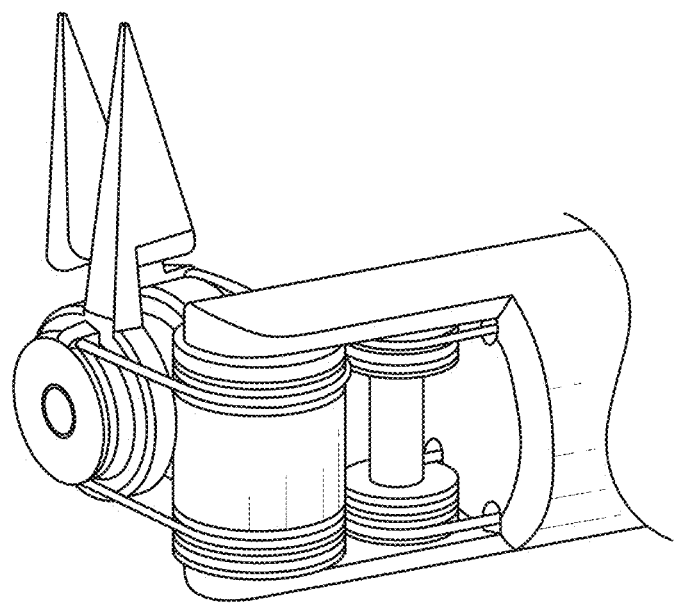
FIG. 19 is a diagram showing an example operation of the surgical tool unit end portion 101.
Figure 20:
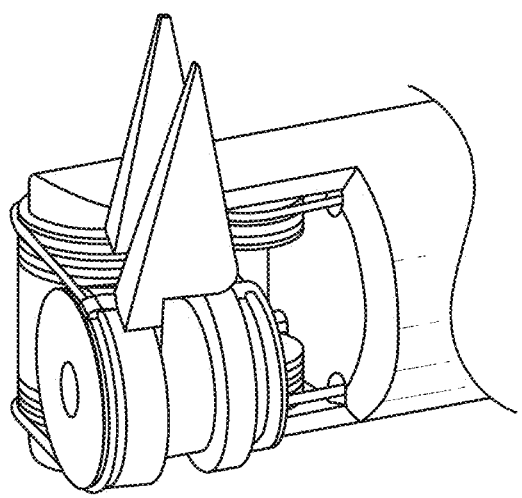
FIG. 20 is a diagram showing an example operation of the surgical tool unit end portion 101.
Figure 21:
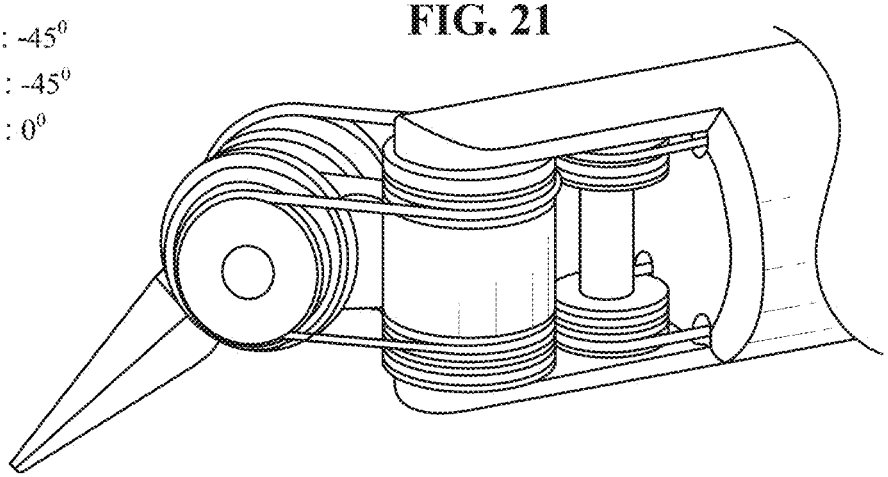
FIG. 21 is a diagram showing an example operation of the surgical tool unit end portion 101.
Figure 22:
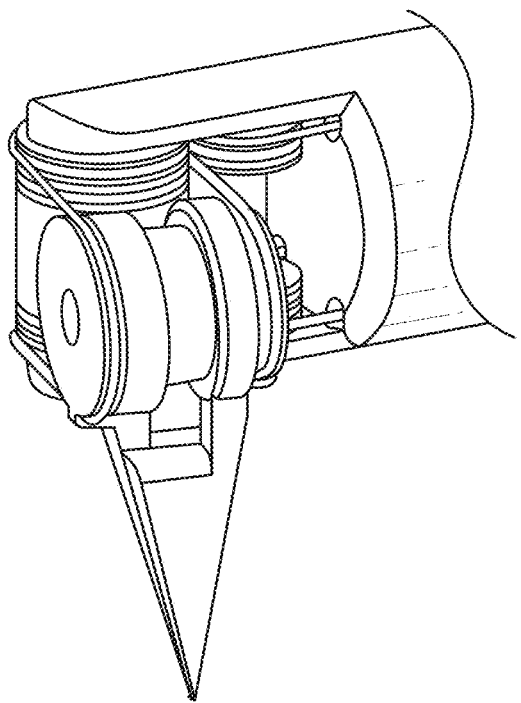
FIG. 22 is a diagram showing an example operation of the surgical tool unit end portion 101.

FIG. 15 shows a state in which the turning angle ψ of the wrist element WE about the first axis is 0 degrees, the turning angle θ of the end effector about the second axis is 0 degrees, and the open angle α of the end effector is 15 degrees. Further, FIG. 16 shows a state in which ψ is 0 degrees, θ is 80 degrees, and a is 15 degrees. Further, FIG. 17 shows a state in which ψ is 0 degrees, θ is 80 degrees, and a is 0 degrees. Further, FIG. 18 shows a state in which ψ is 0 degrees, θ is −80 degrees, and a is 15 degrees. Further, FIG. 19 shows a state in which ψ is −80 degrees, θ is 80 degrees, and a is 15 degrees. Further, FIG. 20 shows a state in which ψ is 80 degrees, θ is 80 degrees, and a is 15 degrees. Further, FIG. 21 shows a state in which ψ is −45 degrees, θ is −45 degrees, and a is 0 degrees. Further, FIG. 22 shows a state in which ψ is 80 degrees, θ is −80 degrees, and a is 0 degrees.

As can be seen from FIGS. 15 to 22, in the surgical tool unit end portion 101, the wrist element WE has a degree of freedom of ±80 degrees about the first axis, and the end effector has a degree of freedom of ±80 degrees about the second axis.

C. Example Configuration (2) of a Surgical Tool Unit

Figure 23:
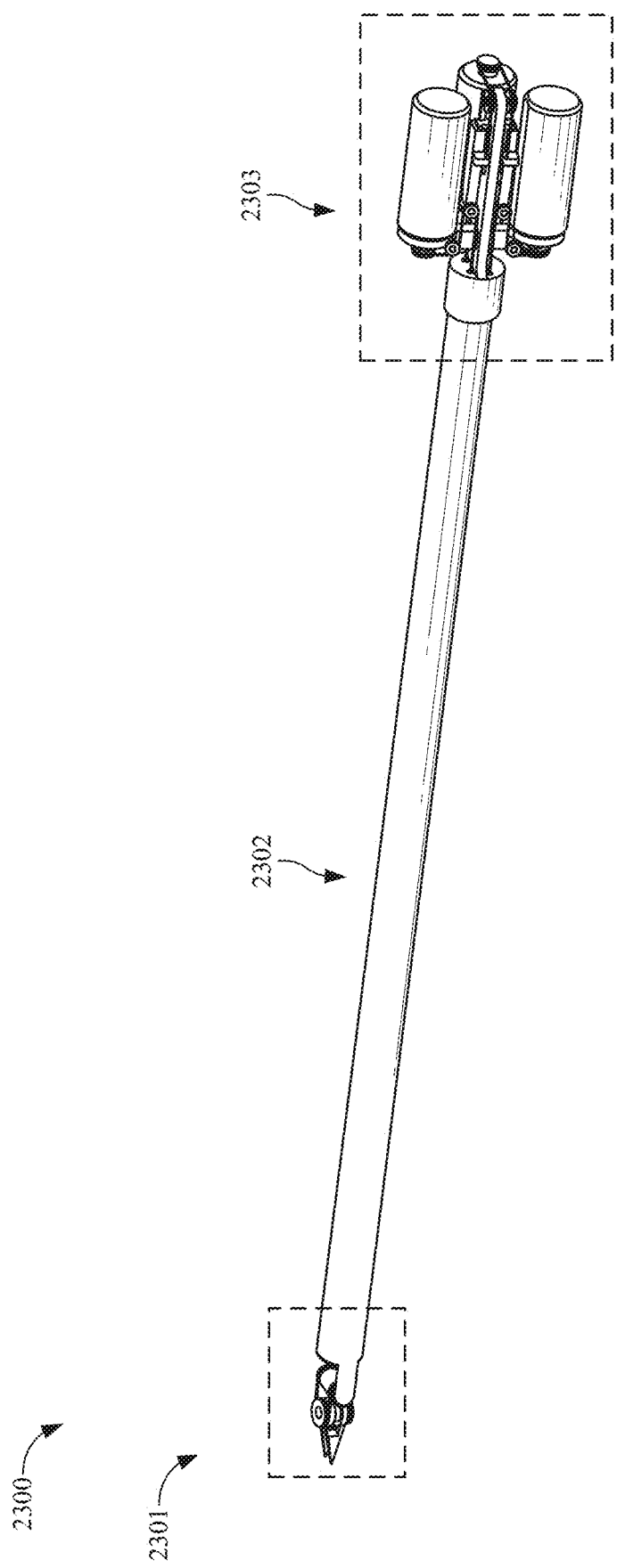
FIG. 23 is a diagram showing an example configuration of a surgical tool unit 2300.

FIG. 23 shows another example configuration of a surgical tool unit to which the technology according to the present disclosure is applied. A surgical tool unit 2300 shown in the drawing includes a hollow shaft 2302 having a longitudinal axis, a surgical tool unit end portion 2301 at one end of the shaft 2302, and a surgical tool unit drive unit 2303 at the other end of the shaft 2302. The surgical tool unit end portion 2301 includes a wrist element capable of turning about a first axis parallel to the yaw axis with respect to the shaft 2302, and an end effector at the end of the wrist element. The end effector performs an opening and closing operation with a second axis functioning as the open-close shaft, the second axis being parallel to the pitch axis. The end effector is formed with a pair of opposing jaw members that turn about the second axis and perform an opening and closing operation. However, the second axis is located at a position offset from the first axis. Meanwhile, the surgical tool unit drive unit 2303 includes two actuators that drive the respective jaw members in the surgical tool unit end portion 2301, and one actuator that drives the wrist.

Figure 24:
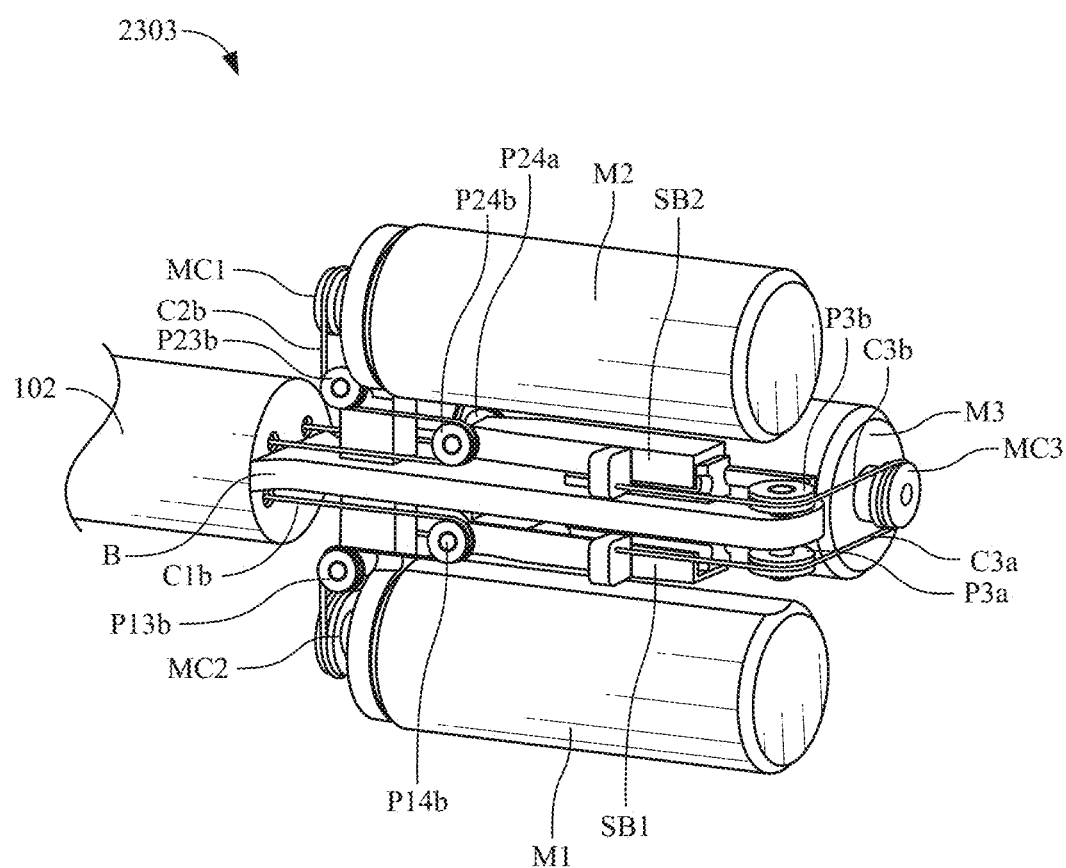
FIG. 24 is an enlarged view of a surgical tool unit drive unit 2303.
Figure 25:
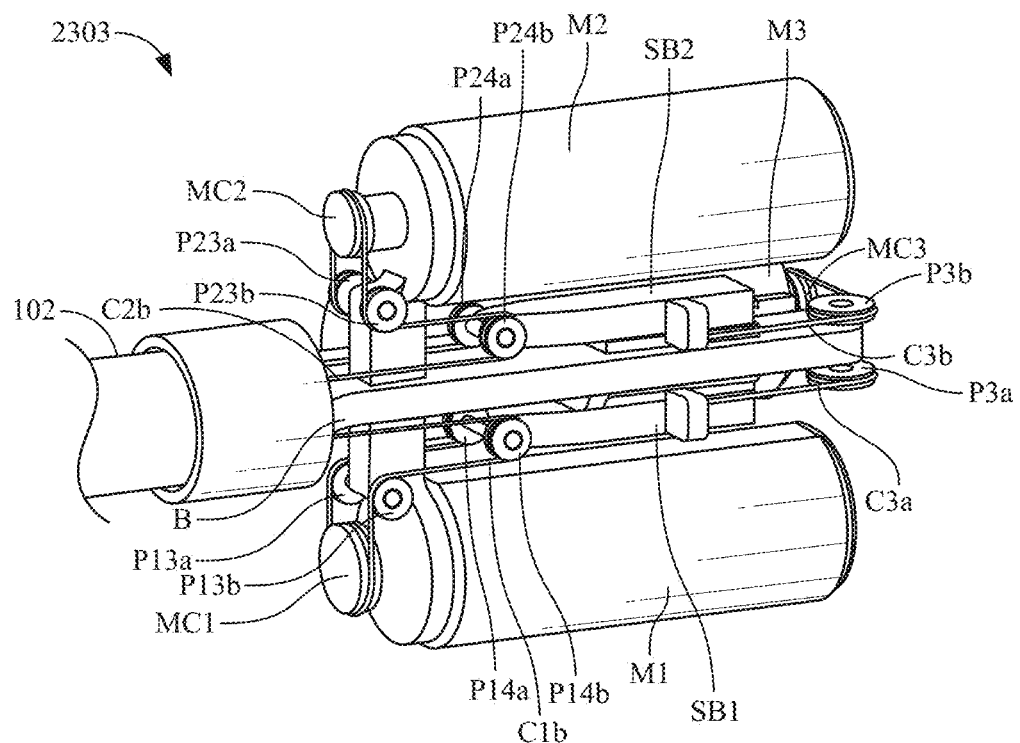
FIG. 25 is an enlarged view of the surgical tool unit drive unit 2303.
Figure 26:
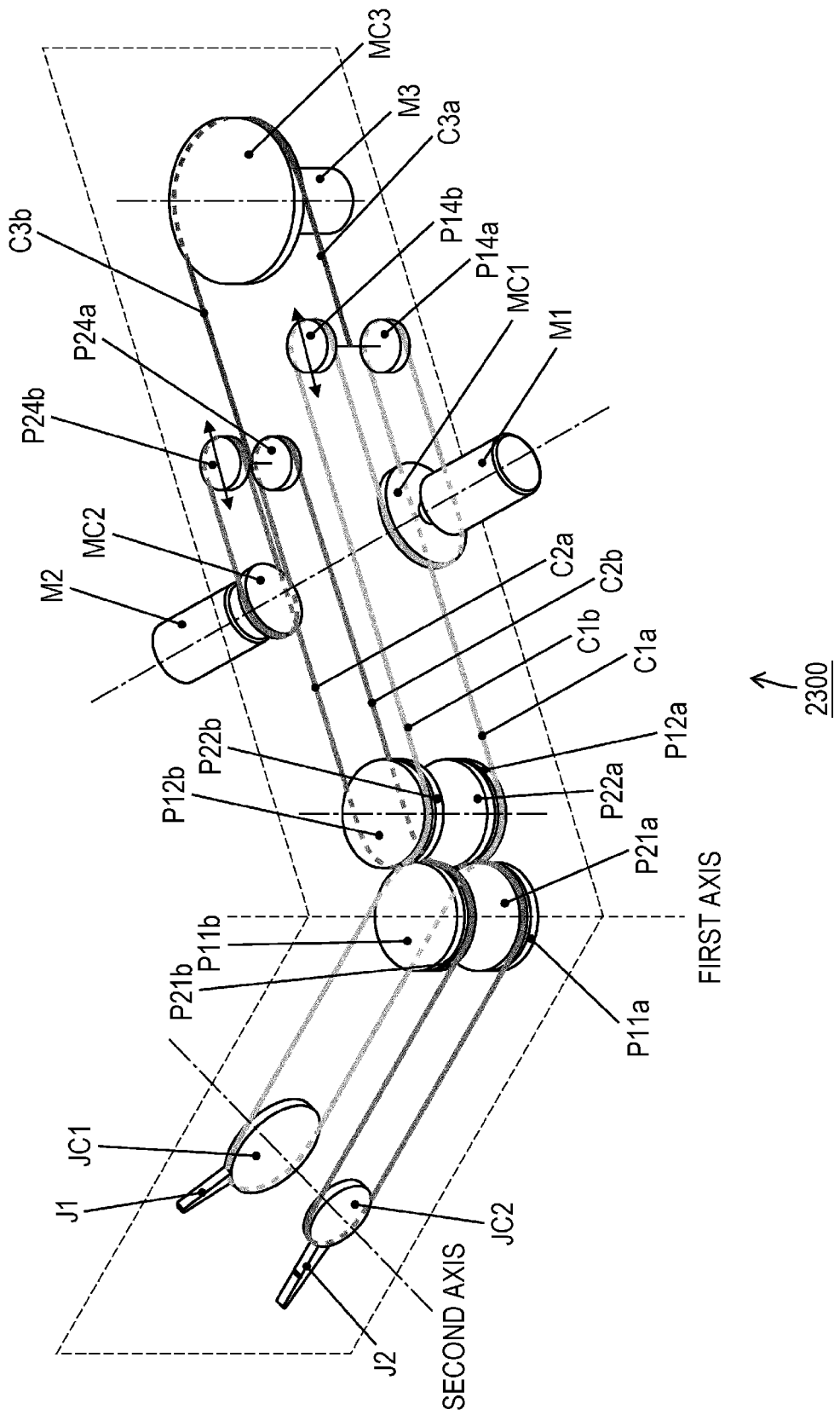
FIG. 26 is a diagram showing an example degree-of-freedom configuration of the surgical tool unit 2300.
Figure 27:
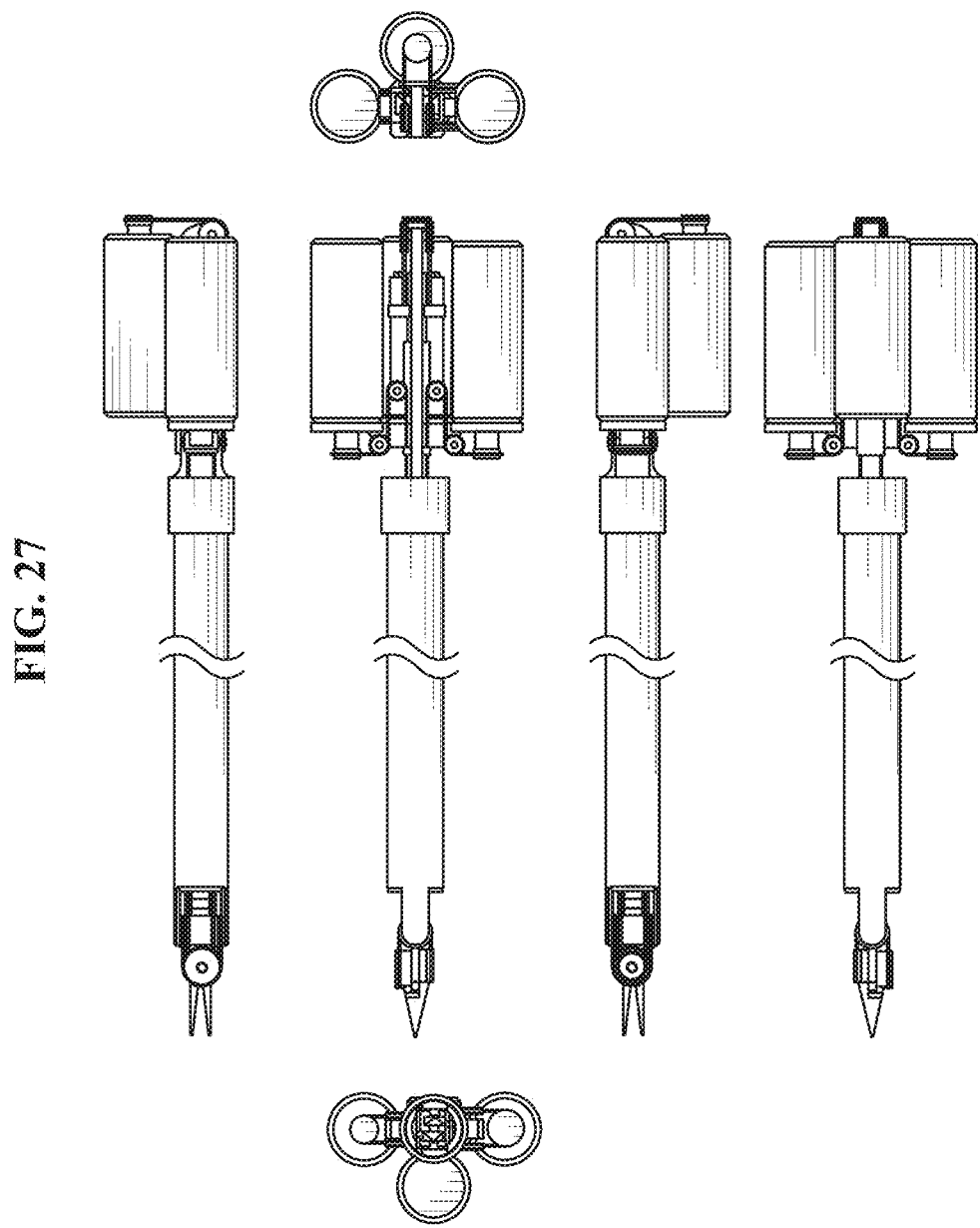
FIG. 27 is a diagram showing a six-sided view of the surgical tool unit 2300.

FIGS. 24 and 25 show the surgical tool unit drive unit 2303 in an enlarged manner (however, the viewing direction is different between FIGS. 24 and 25). Further, FIG. 26 shows an example degree-of-freedom configuration of the surgical tool unit 2300. Furthermore, FIG. 27 shows a six-sided view of the surgical tool unit 2300. Note that the configuration of the surgical tool unit end portion 2301 is similar to that of the surgical tool unit end portion 2301 shown in FIGS. 2 and 3, and therefore, is not shown in these drawings.

Referring to FIG. 26, the surgical tool unit end portion 2301 includes a wrist element WE and an open-close end effector. The end effector includes a pair of opposing jaw members: a first jaw member J1 and a second jaw member J2. The first jaw member J1 is supported by the wrist element WE at a portion near the base, so as to be able to turn about the second axis. Likewise, the second jaw member J2 is supported by the wrist element WE at a portion near the base, so as to be able to turn about the second axis.

A first jaw capstan JC1 having the above-mentioned second axis as its rotation axis is provided near the root of the first jaw member J1. The set of first forward and backward cables C1a and C1b is wound around the first jaw capstan JC1. Also, a second jaw capstan JC2 having the above-mentioned second axis as its rotation axis is provided near the root of the second jaw member J2. The set of second forward and backward cables C2a and C2b is wound around the second jaw capstan JC2.

The first forward cable C1a is pulled in a direction orthogonal to the second axis. However, the direction of the cable C1a is switched to a direction orthogonal to the first axis by a first idler pulley P11a that uses the first axis as its rotation axis, and further, the layout is adjusted so that the first forward cable C1a is inserted through the shaft 2302 by a first adjacent idler pulley P12a that is adjacent to the first idler pulley P11a and has a rotation axis parallel to the first axis. Also, the direction of the first backward cable C1b is switched from a direction orthogonal to the second axis to a direction orthogonal to the first axis by a first idler pulley P11b that uses the first axis as its rotation axis, and further, the layout is adjusted so that the first backward cable C1b is inserted through the shaft 2302 by a first adjacent idler pulley P12b that is adjacent to the first idler pulley P11b and has a rotation axis parallel to the first axis.

Meanwhile, the second forward cable C2a is pulled in a direction orthogonal to the second axis. However, the direction of the cable C2a is switched to a direction orthogonal to the first axis by a second idler pulley P21a that uses the first axis as its rotation axis, and further, the layout is adjusted so that the second forward cable C2a is inserted through the shaft 2302 by a second adjacent idler pulley P22a that is adjacent to the second idler pulley P21a and has a rotation axis parallel to the first axis. Also, the direction of the second backward cable C2b is switched from a direction orthogonal to the second axis to a direction orthogonal to the first axis by a first idler pulley P11b, and further, the layout is adjusted so that the second backward cable C2b is inserted through the shaft 2302 by a second adjacent idler pulley P22b that is adjacent to the second idler pulley P21b and has a rotation axis parallel to the first axis.

Next, the side of the surgical tool unit drive unit 2303 is described, with reference to FIGS. 24 to 26.

The surgical tool unit drive unit 2303 includes a first motor M1 to be used for driving the first jaw member J1, a second motor M2 to be used for driving the second jaw member J2, and a third motor M3 to be used for driving the wrist element WE (see FIGS. 24, 25, and 26, for example). Further, first to third motor capstans MC1, MC2, and MC3 as drive capstans are attached to the respective output shafts of the first to third motors M1 to M3 (see FIG. 26, for example). Although a rotary motor is assumed to be used for each of the first to third motors M1 to M3, a motor with a speed reducer may also be used.

The set of first forward and backward cables C1a and C1b is wound around the first motor capstan MC1. That is, the layout is designed so that power transmission between the first jaw capstan JC1 and the first motor capstan MC1 is performed by the cable loop method. Accordingly, the first motor capstan MC1 is rotated by the first motor M1, so that the rotation of the first jaw capstan JC1 can adjust the turning angle of the first jaw member J1 about the second axis.

Also, the set of second forward and backward cables C2a and C2b is wound around the second motor capstan MC2. That is, the layout is designed so that power transmission between the second jaw capstan JC2 and the second motor capstan MC2 is performed by the cable loop method. Accordingly, the second motor capstan MC2 is rotated by the first motor M2, so that the rotation of the second jaw capstan JC2 can adjust the turning angle of the second jaw member J2 about the second axis.

As already described with reference to FIGS. 2 and 3, each of the first jaw member J1 and the second jaw member J2 is turned about the second axis so that a change is caused in the difference between the angles of the first jaw member J1 and the second jaw member J2 about the second axis. Thus, the end effector is opened and closed. Further, the first jaw member J1 and the second jaw member J2 are simultaneously turned about the second axis so that a change is caused in the sum of the angles of the first jaw member J1 and the second jaw member J2 about the second axis. Thus, the end effector formed with the first jaw member J1 and the second jaw member J2 is turned about the second axis.

Referring to FIGS. 24 and 25, each of the first to third motors M1 to M3 is secured onto a base B integrated with an end (the proximal end) of the shaft 2302. Further, a set of third forward and backward cables C3a and C3b is wound around the third motor capstan MC3 via third idler pulleys P3a and P3b. The other end of the third forward cable C3a is secured to a first slide base SB1 that slides in the longitudinal axis direction of the shaft 102. Also, the other end of the third backward cable C3b is secured to a second slide base SB2 that slides in the longitudinal axis direction of the shaft 102.

In short, the set of third forward and backward cables C3a and C3b is laid out so as to perform power transmission between the third motor capstan MC3, and the first and second slide bases SB1 and SB2. Accordingly, when the third motor capstan MC3 is rotated by the third motor M3, the first slide base SB1 and the second slide base SB2 can be moved forward and backward in opposite directions in the longitudinal axis direction of the shaft 102.

Note that the third forward cable C3a in the section from the first slide base SB1 to the third idler pulley P3a, and the third backward cable C3b in the section from the second slide base SB2 to the third idler pulley P3b are preferably laid out so as to be parallel to the longitudinal axis of the shaft 102.

As can be seen from FIGS. 24 to 26, the first forward cable C1a is wound around the first motor capstan MC1, via an idler pulley P14a on the first slide base SB1. The first backward cable C1b is wound around the first motor capstan MC1 from the opposite direction to the first forward cable C1a, via an idler pulley P14b on the first slide base SB1. Therefore, when the first slide base SB1 is made to move backward to the root side (which is the proximal end) of the shaft 2302, the idler pulleys P14a and P14b also move backward. Accordingly, the set of first forward and backward cables C1a and C1b is pulled toward the proximal end side, and a rotation torque acts on the first jaw member J1.

Also, the second forward cable C2a is wound around the second motor capstan MC2, via an idler pulley P24a on the second slide base SB2. The second backward cable C2b is wound around the second motor capstan MC2 from the opposite direction to the second forward cable C2a, via an idler pulley P24b on the second slide base SB2. Therefore, when the second slide base SB2 is made to move backward, the idler pulleys P24a and P24b also move backward. Accordingly, the set of second forward and backward cables C2a and C2b is pulled toward the proximal end side, and a rotation torque acts on the second jaw member J2.

When the first slide base SB1 is moved forward, and the second slide base SB2 is moved backward, the set of first forward and backward cables C1a and C1a moves forward, and the set of second forward and backward cables C2a and C2b moves forward. As a result, the wrist element WE rotates in the positive direction about the first axis. Conversely, when the first slide base SB1 is moved backward, and the second slide base SB2 is moved forward, the set of first forward and backward cables C1a and C1a moves backward, and the set of second forward and backward cables C2a and C2b moves forward. As a result, the wrist element WE rotates in the negative direction about the first axis. Here, it is assumed that both the set of first forward and backward cables C1a and C1b and the set of second forward and backward cables C2a and C2b have a constant total length.

Figure 28:
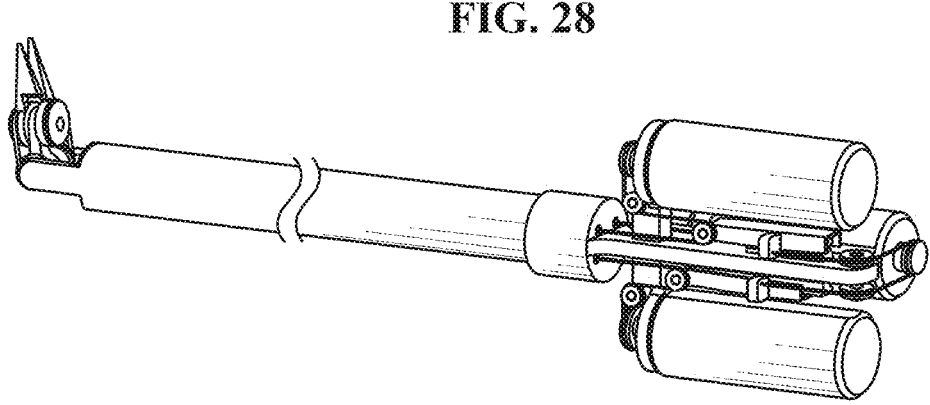
FIG. 28 is a diagram showing a state in which the wrist element WE is turned about the first axis.
Figure 29:
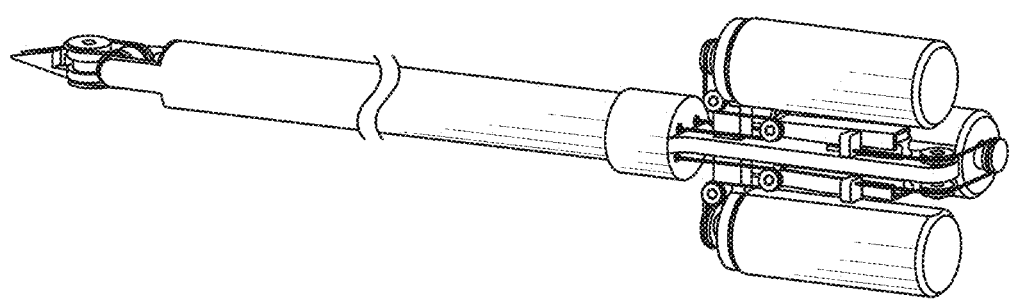
FIG. 29 is a diagram showing a state in which the wrist element WE is turned about the first axis.
Figure 30:
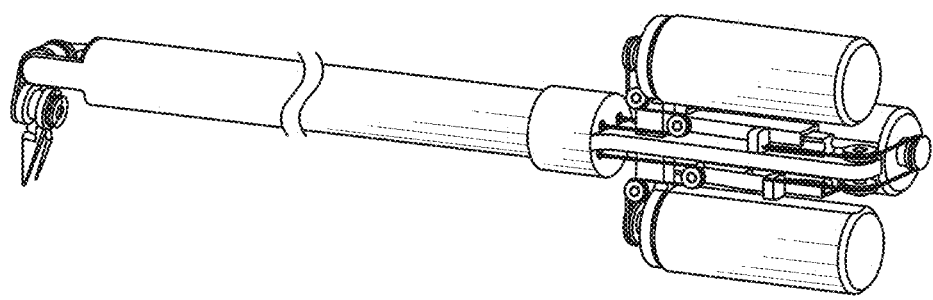
FIG. 30 is a diagram showing a state in which the wrist element WE is turned about the first axis.

FIGS. 28 to 30 each show a state in which the wrist element WE is turned about the first axis by drive of the third motor M3. As can be seen from FIGS. 28 to 30, by the drive of the third motor M3, the first slide base SB1 and the second slide base SB2 move forward and backward in the longitudinal axis direction of the shaft 2302, and pull each cable of the set of first forward and backward cables C1a and C1b and the set of second forward and backward cables C2a and C2b. However, being secured onto the base B, the first motor M1 and the second motor M2 do not slide.

By rotational drive of the third motor M3, the second slide base SB2 is pulled with the third backward cable C3b, and is moved backward to the proximal end side in the longitudinal axis direction of the shaft 2302. The wrist element WE is then pulled by the set of second forward and backward cables C2a and C2b, and rotates 80 degrees about the first axis as shown in FIG. 28.

Further, in a case where the positions of the first slide base SB1 and the second slide base SB2 in the longitudinal axis direction of the shaft 102 are the same, the rotational position of the wrist element WE about the first axis is 0 degrees, as shown in FIG. 29.

Also, by rotational drive of the third motor M3 in the opposite direction, the first slide base SB1 is pulled with the third forward cable C3a, and is moved backward to the proximal end side in the longitudinal axis direction of the shaft 2302. The wrist element WE is then pulled by the set of first forward and backward cables C1a and C1b, and rotates −80 degrees about the first axis as shown in FIG. 30.

In this manner, the third motor M3 pulls the set of third forward and backward cables C3a and C3b, and the set of first forward and backward cables C1a and C1b and the set of second forward and backward cables C2a and C2b are moved forward and backward through sliding operations of the first slide base SB1 and the second slide base SB2. Thus, the wrist element WE can be turned about the first axis. Furthermore, when the wrist element WE is turned about the first axis, the pre-tension of the set of first forward and backward cables C1a and C1b and the set of second forward and backward cables C2a and C2b does not change.

The surgical tool unit 2300 differs from the surgical tool unit 100 shown in FIGS. 1 to 22 in that both the first motor M1 and the second motor M2 are secured to the base, and do not slide during a turning operation of the wrist element WE about the first axis. Thus, inertia of the structure during a sliding operation can be lowered.

The operation methods in the surgical tool unit end portion 2301 are summarized below.

Operation at the First Axis:

When the third motor capstan MC3 is rotated by the third motor M3, a tractive force is generated in one cable of the set of third forward and backward cables C3a and C3b. As a result, the wrist element WE and the end effector mounted on the wrist element WE can be rotated in the positive direction or the reverse direction about the first axis.

Operation at the Second Axis:

The average value of the angle of the first jaw member J1 about the second axis and the angle of the second jaw member J2 about the second axis is defined as the angle of the end effector about the second axis. When the first jaw capstan JC1 and the second jaw capstan JC2 rotate in the same direction and at the same speed, a turning operation of the end effector about the second axis is caused.

Operation of the End Effector:

The end effector is formed with a pair of opposing jaw members: the first jaw member J1 and the second jaw member J2 (see FIG. 2, for example). The open angle of the first jaw member J1 and the second jaw member J2 is set as the open-close angle of the end effector. When the first motor capstan MC1 and the second motor capstan MC2 are rotated in opposite directions at the same speed, an opening and closing operation of the end effector is caused.

Next, the relationship between operations of the first to third motors M1 to M3 and operations of the surgical tool unit end portion 2301 is described.

As shown in FIG. 13, the wrist element WE turns about the first axis. As shown in the drawing, the radius of each of the idler pulleys P11a, P11b, P21a, and P21b that rotate about the first axis is represented by $R_\psi$, and the turning angle of the wrist element WE about the first axis is $\psi$.

Further, as shown in FIG. 14, the first jaw member J1 and the second jaw member J2 each turn about the second axis, so that a turning operation and an opening and closing operation of the end effector are performed. The pulley radius of the first jaw capstan JC1 is represented by $R_{JC1}$, the pulley radius of the second jaw capstan JC2 is $R_{JC2}$, the turning angle of the first jaw member J1 about the second axis is $\theta_{j1}$, the turning angle of the second jaw member J2 about the second axis is $\theta_{j2}$, the open angle of the end effector is $\alpha$, and the turning angle of the end effector about the second axis is $\theta$.

Further, although not shown in the drawing, the pulley radius of the first motor capstan MC1 is represented by $R_{MC1}$, the pulley radius of the second motor capstan MC2 is $R_{MC2}$, the pulley radius of the third motor capstan MC3 is $R_{MC3}$, the rotation angle of the first motor capstan MC1 is $\sigma_{MC1}$, the rotation angle of the second motor capstan MC2 is $\sigma_{MC2}$, and the rotation angle of the third motor capstan MC3 is $\sigma_{MC3}$.

Here, the turning angle $\psi$ of the wrist element WE about the first axis, the turning angle $\theta$ of the end effector about the second axis, and the open angle $\alpha$ of the end effector are expressed as in the following Equations (6) to (8), respectively.

[Mathematical Formula 6]
$$\psi = \frac{2R_{MC3}}{R_\psi}\phi_{MC3} \tag{6}$$

[Mathematical Formula 7]
$$\theta = \frac{\theta_{j1} + \theta_{j2}}{2} \tag{7}$$

[Mathematical Formula 8]
$$\alpha = \theta_{j1} - \theta_{j2} \tag{8}$$

A result of comparison between Equation (6) and Equation (1) relating to the surgical tool unit 100 shows that, in the case of the surgical tool unit 2300, the turning angle $\psi$ of the wrist element WE about the first axis is twice the amount of rotation of the third motor M3. Therefore, the resolution of rotation about the first axis is lowered to ½. This is because the idler pulleys P14a and P14b secured to the first slide base SB1, and the idler pulleys P24a and P24b secured to the second slide base SB2 operate as moving pulleys.

Meanwhile, the turning angle $\theta_{j1}$ of the first jaw member J1 about the second axis, and the turning angle $\theta_{j2}$ of the second jaw member J2 about the second axis are expressed as in the following Equations (9) and (10), respectively.

[Mathematical Formula 9]
$$\theta_{j1} = \frac{R_{MC1}}{R_{JC1}}\phi_{MC1} \tag{9}$$

[Mathematical Formula 10]
$$\theta_{j2} = \frac{R_{MC2}}{R_{JC2}}\phi_{MC2} \tag{10}$$

As can be seen from the above Equations (6) to (10), the turning angle $\psi$ of the wrist element WE about the first axis, the turning angle $\theta$ of the end effector about the second axis, and the open angle $\alpha$ of the end effector can be independently driven without affecting one another. Thus, it can be said that the surgical tool unit 2300 has a structure that does not cause cross-axis interference.

Furthermore, in the surgical tool unit end portion 2301, a turning operation of the wrist element WE about the first axis, a turning operation of the end effector about the second axis, and an opening and closing operation of the end effector are performed, as shown in FIGS. 15 to 22.

D. Example Configuration (3) of a Surgical Tool Unit

Figure 31:
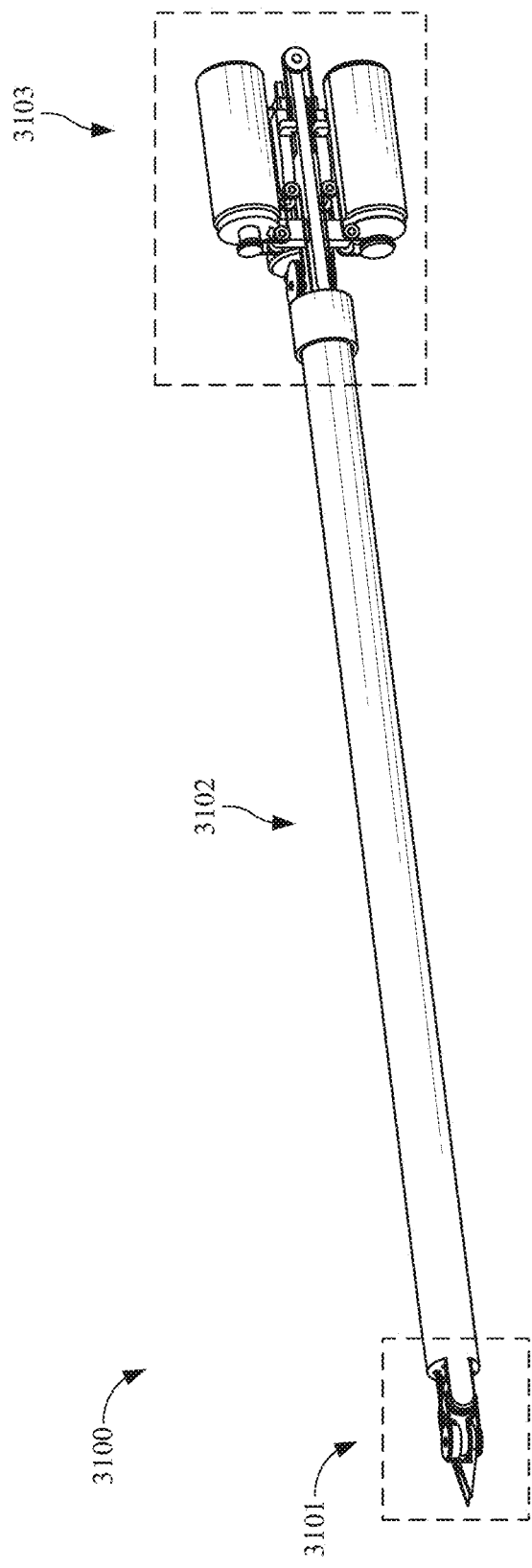
FIG. 31 is a diagram showing an example configuration of a surgical tool unit 3100.

FIG. 31 shows yet another example configuration of a surgical tool unit to which the technology according to the present disclosure is applied. A surgical tool unit 3100 shown in the drawing includes a hollow shaft 3102 having a longitudinal axis, a surgical tool unit end portion 3101 at one end of the shaft 3102, and a surgical tool unit drive unit 3103 at the other end of the shaft 3102. The surgical tool unit end portion 3101 includes a wrist element capable of turning about a first axis parallel to the yaw axis with respect to the shaft 3102, and an end effector at the end of the wrist element. The end effector performs an opening and closing operation with a second axis functioning as the open-close shaft, the second axis being parallel to the pitch axis. The end effector is formed with a pair of opposing jaw members that turn about the second axis and perform an opening and closing operation. However, the second axis is located at a position offset from the first axis. Meanwhile, the surgical tool unit drive unit 3103 includes two actuators that drive the respective jaw members in the surgical tool unit end portion 3101, and one actuator that drives the wrist.

Figure 32:
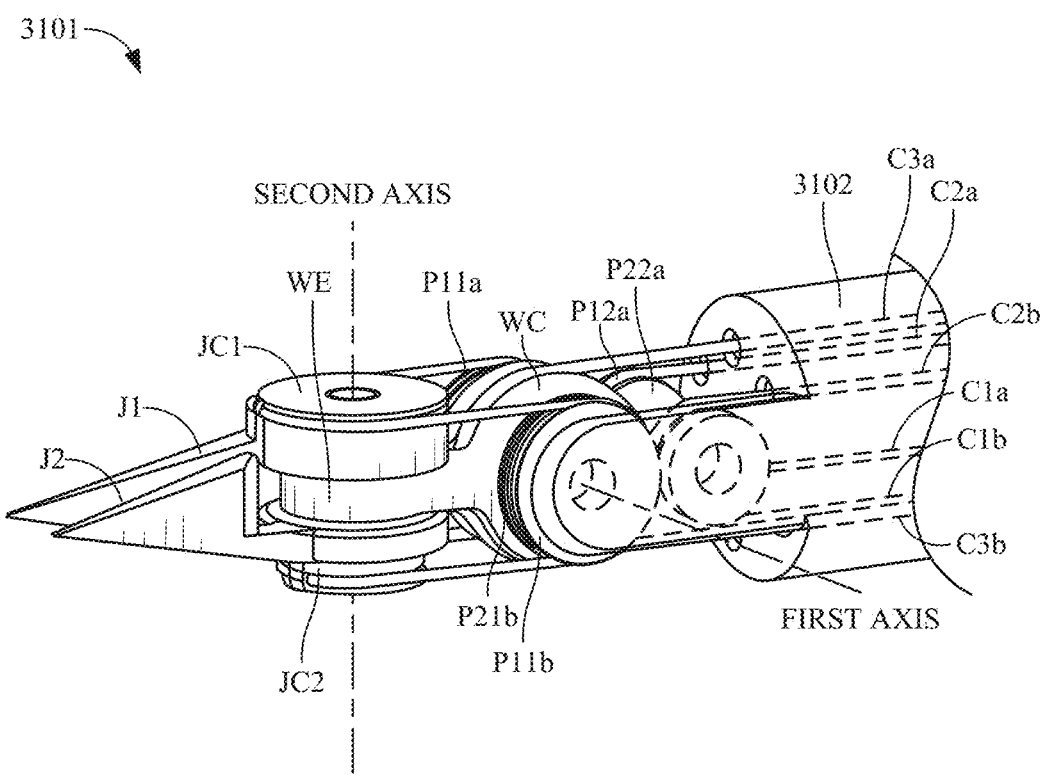
FIG. 32 is an enlarged view of a surgical tool unit end portion 3101.
Figure 33:
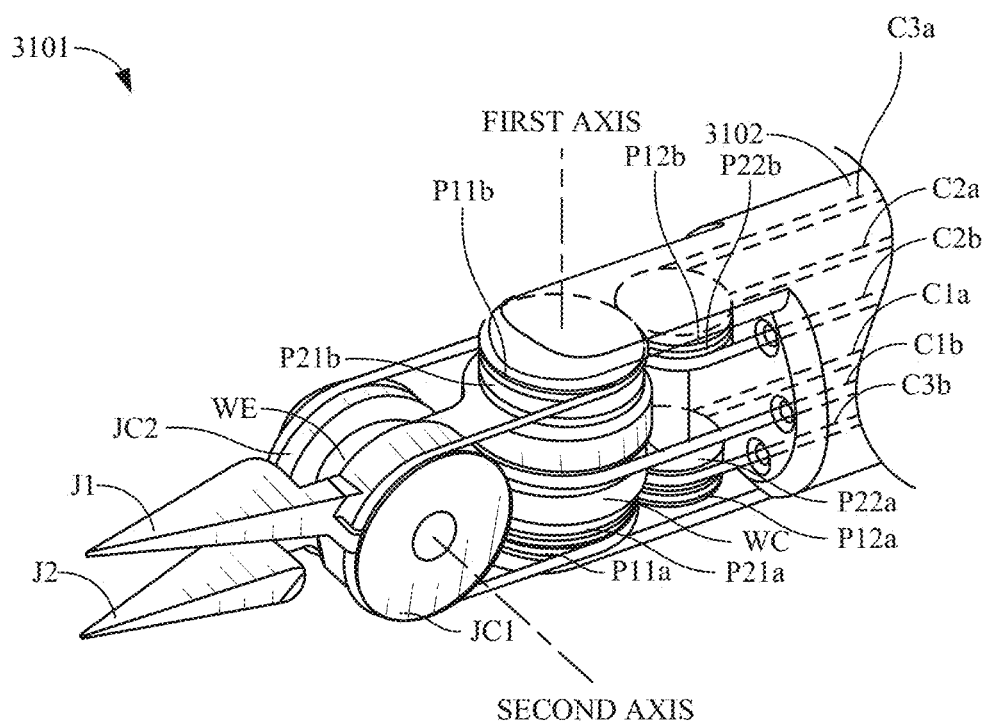
FIG. 33 is an enlarged view of the surgical tool unit end portion 3101.
Figure 34:
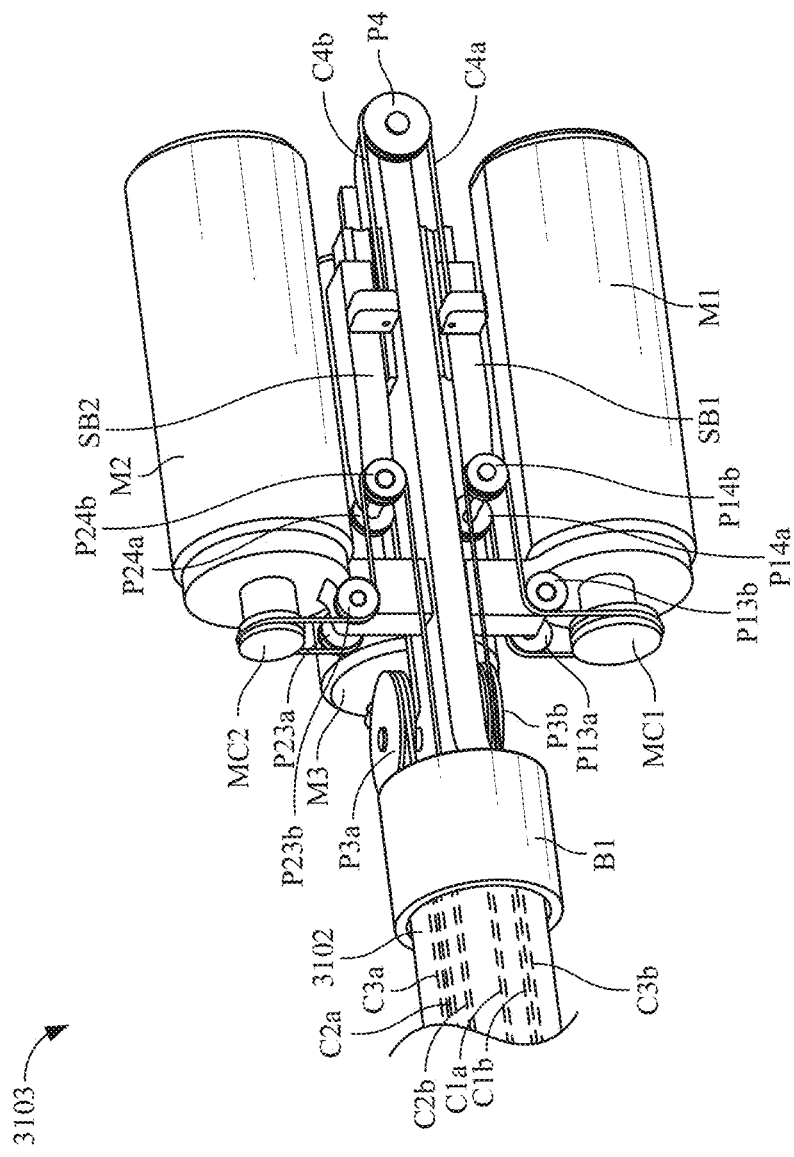
FIG. 34 is an enlarged view of a surgical tool unit drive unit 3103.
Figure 35:
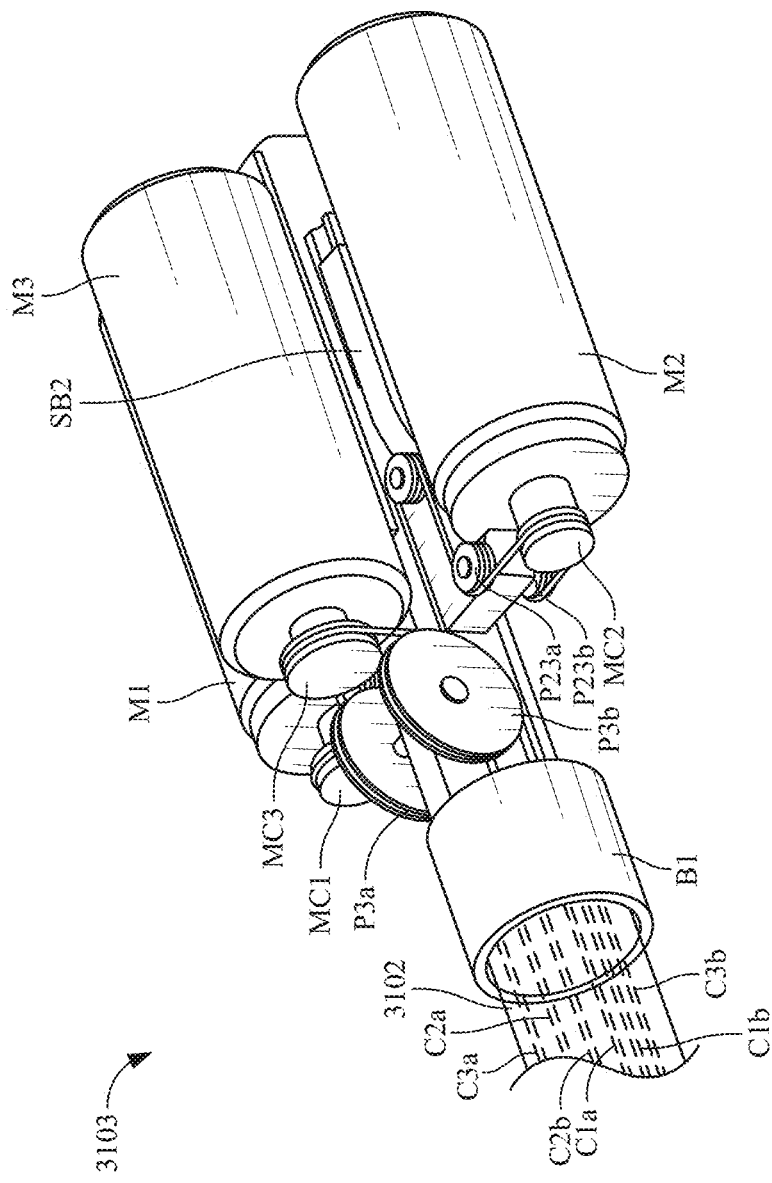
FIG. 35 is an enlarged view of the surgical tool unit drive unit 3103.
Figure 36:
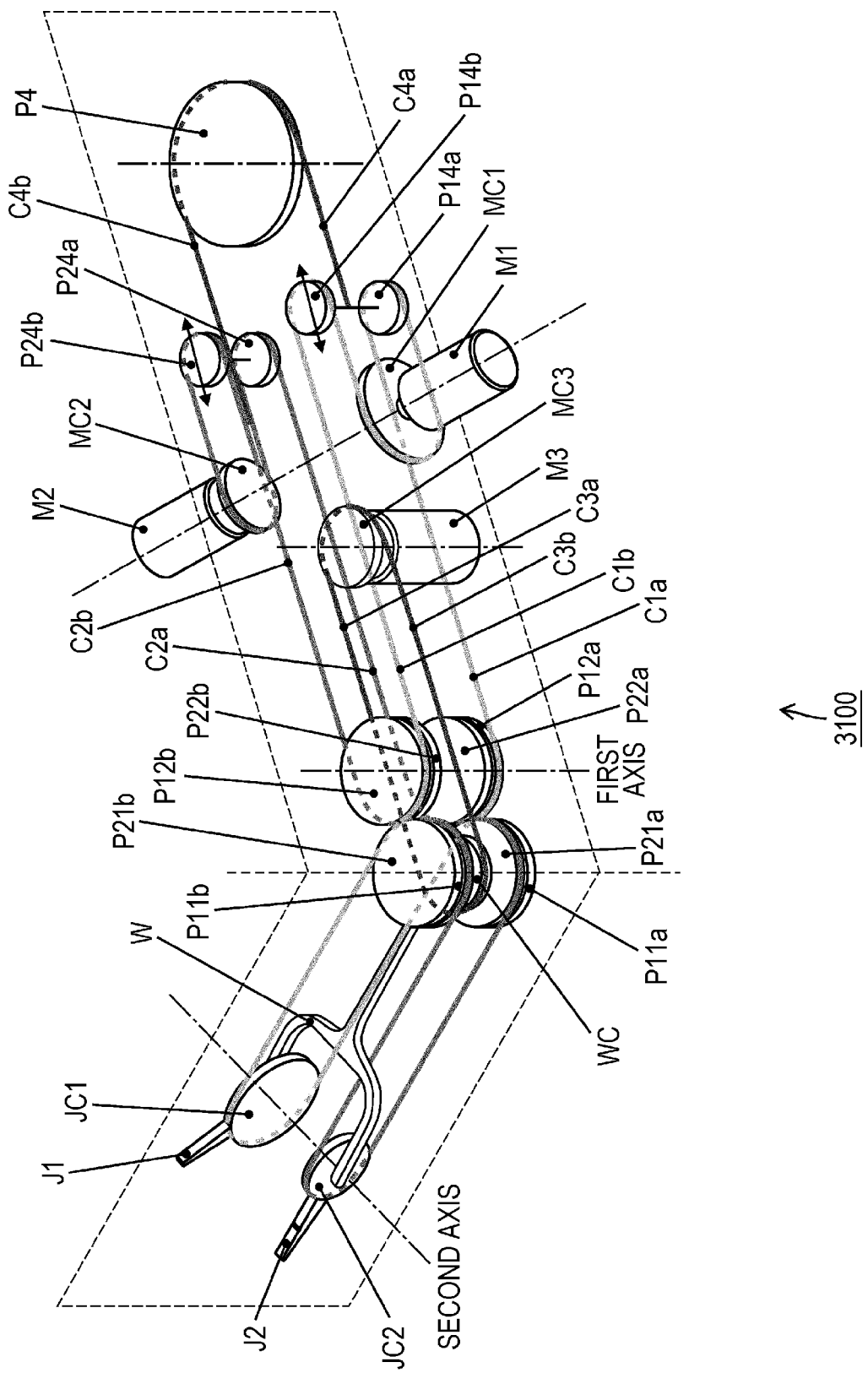
FIG. 36 is a diagram showing an example degree-of-freedom configuration of the surgical tool unit 3100.
Figure 37:
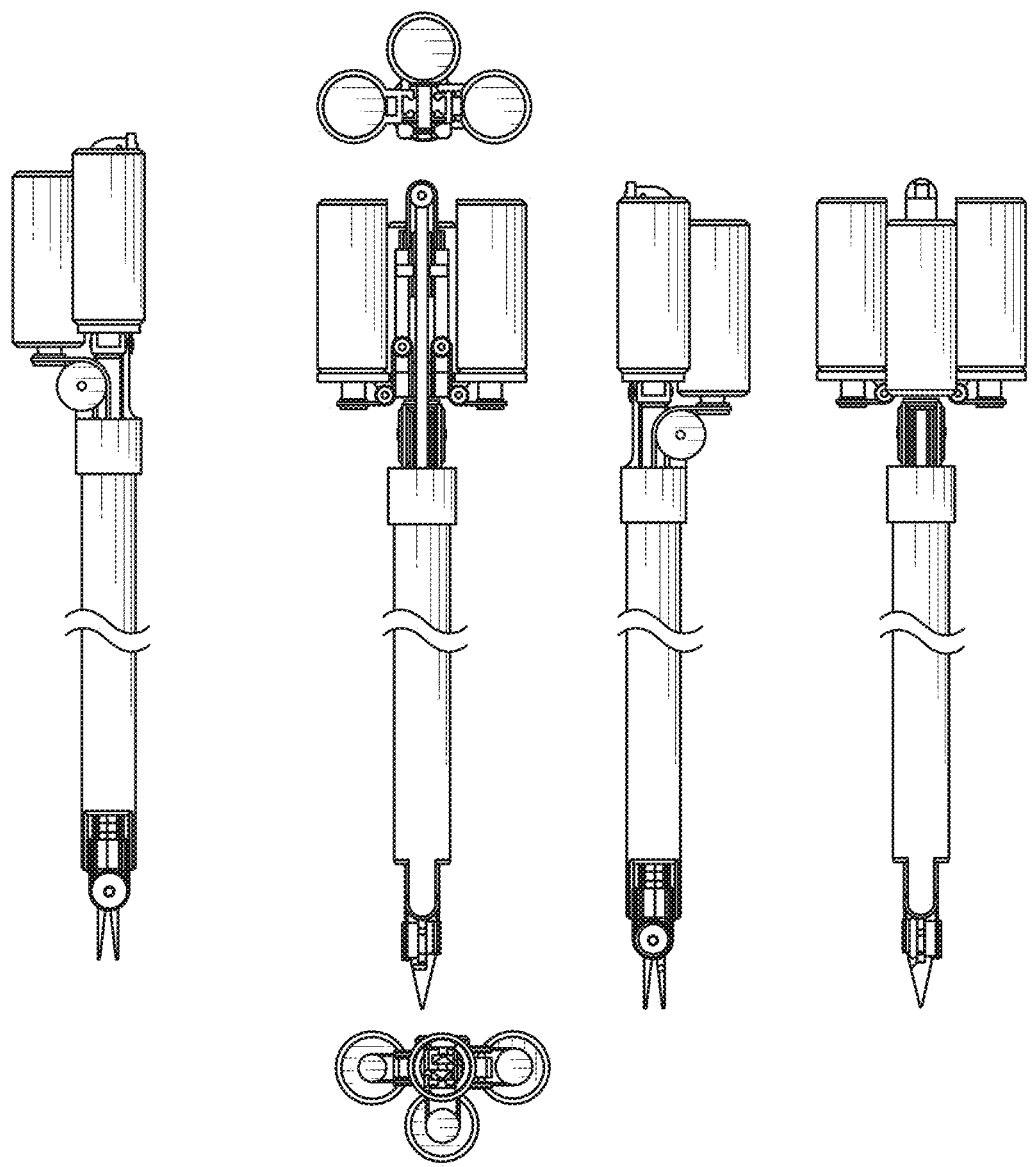
FIG. 37 is a diagram showing a six-sided view of the surgical tool unit 3100.

FIGS. 32 and 33 show the surgical tool unit end portion 3101 in an enlarged manner (however, the viewing direction is different between FIGS. 32 and 33). Also, FIGS. 34 and 35 show the surgical tool unit drive unit 3103 in an enlarged manner (however, the viewing direction is different between FIGS. 34 and 35). Further, FIG. 36 shows an example degree-of-freedom configuration of the surgical tool unit 3100. Furthermore, FIG. 37 shows a six-sided view of the surgical tool unit 3100.

The surgical tool unit end portion 3101 includes a wrist element WE and an open-close end effector. The end effector includes a pair of opposing jaw members: a first jaw member J1 and a second jaw member J2 (see FIGS. 32 and 33, for example). The wrist element WE is supported at a portion near the root so as to be able to turn about the first axis parallel to the yaw axis at the end (distal end) of the shaft 3102. Further, the first jaw member J1 and the second jaw member J2 that constitute the end effector are supported so as to be able to turn about the second axis parallel to the pitch axis at the end of the wrist element WE. The first jaw member J1 and the second jaw member J2 open and close when the open angle with the second axis serving as the open-close shaft changes.

Meanwhile, the surgical tool unit drive unit 3103 includes a first motor M1 to be used for driving the first jaw member J1, a second motor M2 to be used for driving the second jaw member J2, and a third motor M3 to be used for driving the wrist element WE (see FIGS. 34, 35, and 36, for example). Each of the first to third motors M1 to M3 is secured onto a base B1 integrated with an end (the proximal end) of the shaft 3102. Further, first to third motor capstans MC1, MC2, and MC3 as drive capstans are attached to the output shafts of the first to third motors M1 to M3, respectively. Although a rotary motor is assumed to be used for each of the first to third motors M1 to M3, a motor with a speed reducer may also be used.

Referring to FIGS. 34 and 35, a first slide base SB1 and a second slide base SB2 that slide in the longitudinal axis direction of the shaft 3102 are attached to each side surface of the base B1.

Referring to FIGS. 32, 33, and 36, a first jaw capstan JC1 having the second axis as its rotation axis is provided near the root of the first jaw member J1. The set of first forward and backward cables C1a and C1b is wound around the first jaw capstan JC1. Also, referring to FIGS. 34 to 36, the set of first forward and backward cables C1a and C1b is wound around the first motor capstan MC1.

Referring to FIGS. 32, 33, and 36, the first forward cable C1a is pulled in a direction orthogonal to the second axis. However, the direction of the cable C1a is switched to a direction orthogonal to the first axis by a first idler pulley P11a that uses the first axis as its rotation axis, and further, the layout is adjusted so that the first forward cable C1a is inserted through the shaft 3102 by a first adjacent idler pulley P12a that is adjacent to the first idler pulley P11a and has a rotation axis parallel to the first axis. After inserted through the shaft 3102, the first forward cable C1a is then wound around the first motor capstan MC1 via an idler pulley P14a secured to the first slide base SB1 and an idler pulley P13a secured to the base B1, as shown in FIGS. 34 and 35.

Meanwhile, the first backward cable C1b is pulled in a direction orthogonal to the second axis. However, the direction of the cable C1b is switched to a direction orthogonal to the first axis by a first idler pulley P11b that uses the first axis as its rotation axis, and further, the layout is adjusted so that the first backward cable C1b is inserted through the shaft 3102 by a first adjacent idler pulley P12b that is adjacent to the first idler pulley P11b and has a rotation axis parallel to the first axis. After inserted through the shaft 3102, the first backward cable C1b is then wound around the first motor capstan MC1 from the opposite direction to the first forward cable C1a via an idler pulley P14b secured to the first slide base SB1 and an idler pulley P13b secured to the base B1, as shown in FIGS. 34 and 35.

Accordingly, the first motor capstan MC1 is rotated by the first motor M1, so that a tractive force is generated in the set of first forward and backward cables C1a and C1b. Thus, the rotation of the first jaw capstan JC1 can adjust the turning angle of the first jaw member J1 about the second axis. As the first jaw member J1 is driven by the cable loop method using the set of first forward and backward cables C1a and C1b, it is possible to make the range of movement of the first jaw member J1 wider.

Referring to FIGS. 32, 33, and 36, a second jaw capstan JC2 having the second axis as its rotation axis is provided near the root of the second jaw member J2. The set of second forward and backward cables C2a and C2b is wound around the second jaw capstan JC2. Also, referring to FIGS. 34 to 36, the set of second forward and backward cables C2a and C2b is wound around the second motor capstan MC2.

Referring to FIGS. 32, 33, and 36, the second forward cable C2a is pulled in a direction orthogonal to the second axis. However, the direction of the cable C2a is switched to a direction orthogonal to the first axis by a second idler pulley P21a that uses the first axis as its rotation axis, and further, the layout is adjusted so that the second forward cable C2a is inserted through the shaft 3102 by a second adjacent idler pulley P22a that is adjacent to the second idler pulley P21a and has a rotation axis parallel to the first axis. After inserted through the shaft 3102, the second forward cable C2a is then wound around the second motor capstan MC2 via an idler pulley P24a secured to the second slide base SB2 and an idler pulley P23a secured to the base B1, as shown in FIGS. 34 and 35.

Meanwhile, the second backward cable C2b is pulled in a direction orthogonal to the second axis. However, the direction of the cable C2b is switched to a direction orthogonal to the first axis by a second idler pulley P21b that uses the first axis as its rotation axis, and further, the layout is adjusted so that the second backward cable C2b is inserted through the shaft 3102 by a first adjacent idler pulley P22b that is adjacent to the second idler pulley P21b and has a rotation axis parallel to the first axis. After inserted through the shaft 3102, the second backward cable C2b is then wound around the second motor capstan MC2 from the opposite direction to the second forward cable C2a via an idler pulley P24b secured to the second slide base SB2 and an idler pulley P23b secured to the base B1, as shown in FIGS. 34 and 35.

Accordingly, the second motor capstan MC2 is rotated by the second motor M2, so that a tractive force is generated in the set of second forward and backward cables C2a and C2b. Thus, the rotation of the second jaw capstan JC2 can adjust the turning angle of the second jaw member J2 about the second axis. As the second jaw member J2 is driven by the cable loop method using the set of second forward and backward cables C2a and C2b, it is possible to make the range of movement of the second jaw member J2 wider.

Referring to FIGS. 32, 33, and 36, a wrist capstan WC using the first axis as its rotation axis is provided near the root of the wrist element WE. The set of third forward and backward cables C3a and C3b is wound around the wrist capstan WC. Also, referring to FIGS. 34 to 36, the set of third forward and backward cables C3a and C3b is wound around the third motor capstan MC3.

The tractive force of the set of first forward and backward cables C1a and C1b and the set of second forward and backward cables C2a and C2b is controlled by the first motor M1 and the second motor M2 so that a change is caused in the difference between the angles of the first jaw member J1 and the second jaw member J2 about the second axis. Thus, an opening and closing operation of the end effector formed with the pair of jaw members J1 and J2 can be performed. The open-close angle is determined by the difference between the angles of the first jaw member J1 and the second jaw member J2 about the second axis.

Also, the tractive force of the set of first forward and backward cables C1a and C1b and the set of second forward and backward cables C2a and C2b is controlled by the first motor M1 and the second motor M2 so that a change is caused in the sum of the angles of the first jaw member J1 and the second jaw member J2 about the second axis. Thus, the end effector can be made to turn about the second axis. The average value of the angles of the first jaw member J1 and the second jaw member J2 about the second axis is the turning angle of the end effector about the second axis.

Referring to FIGS. 32, 33, and 36, the third forward cable C3a is wound around the wrist capstan WC, is pulled in a direction orthogonal to the first axis and in the longitudinal axis direction of the shaft 3102, and is inserted through the shaft 3102. After inserted through the shaft 3102, the third forward cable C3a is then wound around the third motor capstan MC3 via a third idler pulley P3a secured to the base B1, as shown in FIGS. 34 and 35.

Meanwhile, the third backward cable C3b is wound around the wrist capstan WC from the opposite direction to the third forward cable C3a, is pulled in a direction orthogonal to the first axis and in the longitudinal axis direction of the shaft 3102, and is inserted through the shaft 3102. After inserted through the shaft 3102, the third backward cable C3b is then wound around the third motor capstan MC3 from the opposite direction to the third forward cable C3a via a third idler pulley P3b secured to the base B1 as shown in FIGS. 34 and 35.

Accordingly, the third motor capstan MC3 is rotated by the third motor M3, so that a tractive force is generated in the set of third forward and backward cables C3a and C3b. Thus, the rotation of the wrist capstan WC can adjust the turning angle of the wrist element WE about the first axis. As the wrist element WE is driven by the cable loop method using the set of third forward and backward cables C3a and C3b, it is possible to widen the range of movement of the wrist element WE.

Referring to FIGS. 34 to 36, a set of fourth forward and backward cables C4a and C4b is wound around a fourth idler pulley P4 secured to the base B1. Further, an end of the fourth forward cable C4a is secured to the first slide base SB1, and the fourth backward cable C4b is secured to the second slide base SB2.

As already described, both the first slide base SB1 and the second slide base SB2 slide on the base B1 in the longitudinal axis direction of the shaft 3102. Further, the idler pulleys P14a and P14b around which the set of first forward and backward cables C1a and C1b is wound are secured to the first slide base SB1, and the set of second forward and backward cables C2a and C2b is secured to the second slide base SB2.

The set of first forward and backward cables C1a and C1b is pulled by the first motor M1, when the first jaw member J1 is turned about the second axis. Also, the set of second forward and backward cables C2a and C2b is pulled by the second motor M2, when the second jaw member J2 is turned about the second axis. Here, when the wrist element WE is turned about the first axis, it is necessary to prevent a load from being applied onto the set of first forward and backward cables C1a and C1b and the set of second forward and backward cables C2a and C2b.

Therefore, the idler pulleys P14a and P14b around which the set of first forward and backward cables C1a and C1b is wound are secured to the first slide base SB1, and the idler pulleys P24a and P24b around which the set of second forward and backward cables C2a and C2b is wound are secured to the second slide base SB2. Further, the set of fourth forward and backward cables C4a and C4b having the respective ends secured to the first slide base SB1 and the second slide base SB2 is wound around the fourth idler pulley P4 secured to the base B1. In this configuration, the first slide base SB1 and the second slide base SB2 move forward and backward in the longitudinal axis direction of the shaft 3102, so that the positions of the idler pulleys P14a and P14b and the idler pulleys P24a and P24b are appropriately adjusted. As a result, when the wrist element WE is turned about the first axis, it is possible to prevent a load from being applied onto the set of first forward and backward cables C1a and C1b and the set of second forward and backward cables C2a and C2b.

When a turning operation about the first axis is actively performed by the wrist element WE as the third motor M3 rotates, the first slide base SB1 and the second slide base SB2 passively move forward and backward accordingly in the longitudinal direction of the shaft 3102. Thus, the tension to be applied onto each cable of the set of first forward and backward cables C1a and C1b and the set of second forward and backward cables C2a and C2b can be kept constant.

The surgical tool unit 3100 is designed to directly rotate the wrist capstan WC with the third motor M3. Accordingly, it is possible to avoid the decrease in resolution of rotation about the first axis in the surgical tool unit 2300 shown in FIGS. 23 to 30.

Further, like the surgical tool unit 2300, the surgical tool unit 3100 has a structure in which both the first motor M1 and the second motor M2 are secured to the base, and do not slide during a turning operation of the wrist element WE about the first axis. Thus, inertia of the structure during a sliding operation can be lowered.

Figure 38:
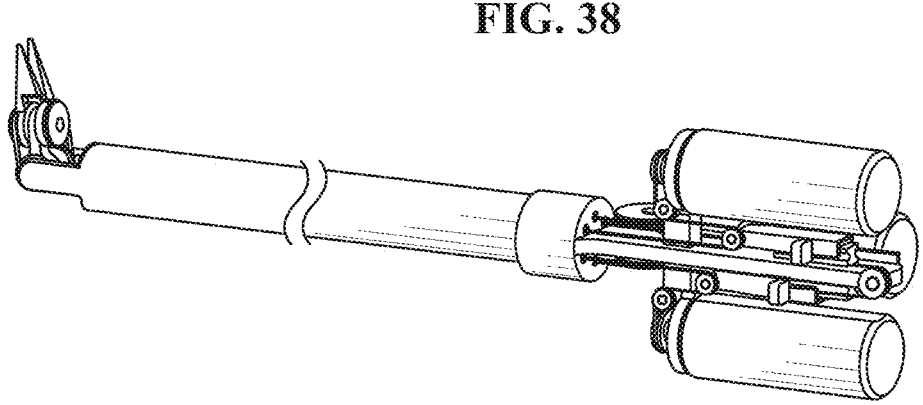
FIG. 38 is a diagram showing a state in which the wrist element WE is turned about the first axis.
Figure 39:
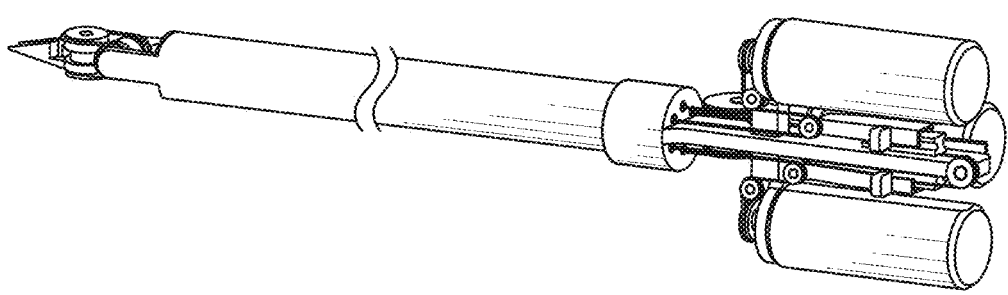
FIG. 39 is a diagram showing a state in which the wrist element WE is turned about the first axis.
Figure 40:
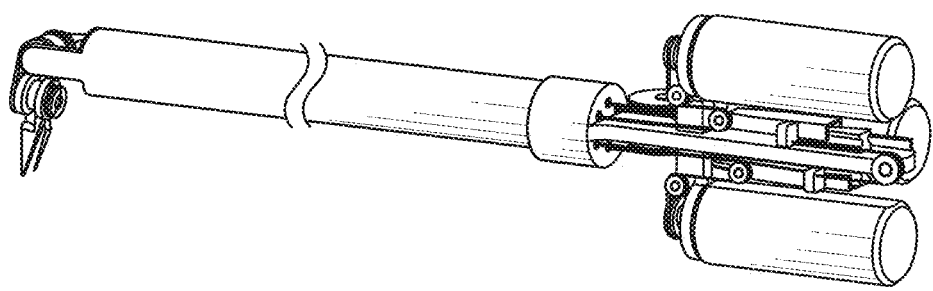
FIG. 40 is a diagram showing a state in which the wrist element WE is turned about the first axis.

FIGS. 38 to 40 each show a state in which the wrist element WE is turned about the first axis by drive of the third motor M3. As can be seen from FIGS. 28 to 30, by the drive of the third motor M3, the first slide base SB1 and the second slide base SB2 move forward and backward in the longitudinal axis direction of the shaft 2302, and pull each cable of the set of first forward and backward cables C1a and C1b and the set of second forward and backward cables C2a and C2b. However, being secured onto the base B, the first motor M1 and the second motor M2 do not slide.

The surgical tool unit 3100 is designed to directly rotate the wrist capstan WC with the third motor M3. By rotational drive of the third motor M3, the wrist element WE is pulled with the third forward cable C3a, and rotates 80 degrees about the first axis as shown in FIG. 38. At that time, the first slide base SB1 moves forward in the longitudinal axis direction of the shaft 3102, and the second slide base SB2 moves backward. As a result, the positions of the idler pulleys P14a and P14b and the idler pulleys P24a and P24b are appropriately adjusted, and a load can be prevented from being applied onto the set of first forward and backward cables C1a and C1b and the set of second forward and backward cables C2a and C2b.

Further, when the rotational position of the wrist element WE about the first axis is 0 degrees, the positions of the first slide base SB1 and the second slide base SB2 in the longitudinal axis direction of the shaft 102 are the same, as shown in FIG. 39. As a result, the positions of the idler pulleys P14a and P14b and the idler pulleys P24a and P24b are appropriately adjusted, and a load can be prevented from being applied onto the set of first forward and backward cables C1a and C1b and the set of second forward and backward cables C2a and C2b.

Also, by rotational drive of the third motor M3, the wrist element WE is pulled with the third forward cable C3a, and rotates −80 degrees about the first axis as shown in FIG. 40. At that time, the second slide base SB2 moves forward in the longitudinal axis direction of the shaft 3102, and the first slide base SB1 moves backward. As a result, the positions of the idler pulleys P14a and P14b and the idler pulleys P24a and P24b are appropriately adjusted, and a load can be prevented from being applied onto the set of first forward and backward cables C1a and C1b and the set of second forward and backward cables C2a and C2b.

As can be seen from FIGS. 38 to 40, the set of third forward and backward cables C3a and C3b is pulled by the third motor M3, so that the wrist element WE can be directly turned about the first axis. When the wrist element WE turns about the first axis, the set of first forward and backward cables C1a and C1b and the set of second forward and backward cables C2a and C2b then move forward and backward in the longitudinal axis direction of the shaft 3102. Thus, the pre-tension of the set of first forward and backward cables C1a and C1b and the set of second forward and backward cables C2a and C2b does not change.

The operation methods in the surgical tool unit end portion 3101 are summarized below.

Operation at the First Axis:

When the third motor capstan MC3 is rotated by the third motor M3, a tractive force is generated in one cable of the set of third forward and backward cables C3a and C3b. As a result, the wrist element WE and the end effector mounted on the wrist element WE can be rotated in the positive direction or the reverse direction about the first axis.

Operation at the Second Axis:

The average value of the angle of the first jaw member J1 about the second axis and the angle of the second jaw member J2 about the second axis is defined as the angle of the end effector about the second axis. When the first jaw capstan JC1 and the second jaw capstan JC2 rotate in the same direction and at the same speed, a turning operation of the end effector about the second axis is caused.

Operation of the End Effector:

The end effector is formed with a pair of opposing jaw members: the first jaw member J1 and the second jaw member J2 (see FIG. 32, for example). The open angle of the first jaw member J1 and the second jaw member J2 is set as the open-close angle of the end effector. When the first motor capstan MC1 and the second motor capstan MC2 are rotated in opposite directions at the same speed, an opening and closing operation of the end effector is caused.

E. Modifications of the Surgical Tool Unit

E-1. Modifications of the Method for Driving the Cables

It is most preferable to use electromagnetic rotary motors as the first to third motors M1 to M3. However, it is also possible to use some other types of actuators capable of rotating the drive capstans. Examples of other modifications of the actuators that pull the cables may include the following.

Piezoelectric linear-motion ultrasonic motors
Piezoelectric rotary ultrasonic motors
Hydraulic linear motors
Hydraulic rotary motors
Polymeric linear actuators
Electromagnetic linear motors
Shape-memory alloys Further, regardless of which kind of actuator is adopted, the actuators may be equipped with a speed reducer, a position detector, and an emergency brake mechanism. Here, examples of the speed reducers include gear reducers, wave gear reducers, planetary gear reducers, paradox planetary gear reducers, cable reducers, traction reducers, ball screws, sliding screws, and worm gears. Further, examples of the position detectors include magnetic encoders, optical encoders, and potentiometers.

E-2. Modifications of the Shape of the Jaw Members

In each of the drawings, the first jaw member J1 and the second jaw member J2 are drawn in simple shapes for convenience sake. In practice, the shape of the jaw members may be changed depending on the purpose of use of the surgical tool unit. For example, the following forms can be adopted.

Forceps
Bipolar forceps
Scissors
Staplers

E-3. Modifications of the Shaft

The shaft 102 is ideally a rigid body, but may have a flexible configuration. Further, in each drawing, the shaft 102 having a simple hollow cylindrical shape is shown for simplification. However, the shaft does not necessarily have a cylindrical shape. For example, a cross-section of the shaft 102 may have a polygonal shape or an elliptical shape, or its cross-sectional shape may change midway in the longitudinal axis direction. The same applies to the shafts 2302 and 3102.

E-4. Modifications of the Cables

A cable may be a bundle of metallic wires, a bundle of resin, or a mixture of a plurality of materials such as metal wires and resin. Also, a shaft 102 formed with a metal having a high rigidity may be used at a cable portion that is disposed inside the shaft 102 or the like and does not need to be curved, and be connected to a flexible cable that is used at a portion having a curve. In this manner, one cable may be formed. Examples of substitutes for the cables include the following.

Metallic or resin wires
Wires obtained by weaving thin metallic or resin wires having a small diameter E-5. Modifications of the Idler Pulleys In the examples described above, idler pulleys are used for adjusting the layout of the cables. With the use of idler pulleys, the sliding friction at a time when the cables are pulled can be reduced, and a smooth operation can be performed. In a case where sliding friction is to be reduced, idler pulleys each having a rotational bearing may be used.

However, the use of idler pulleys adds to the size of the mechanism, and the number of components becomes larger. Therefore, to further reduce the size of the surgical tool unit end portion 101, cables may be laid out along guide grooves formed in the mechanism without any idler pulley.

E-6. Sensing

To detect the tension of the cables, a strain sensor may be mounted on each cable. Examples of the strain sensor include a variable-resistance strain sensor and a fiber Bragg grating (FBG) strain sensor. Alternatively, a torque sensor may be mounted on the actuators that pull cables.

F. Example Applications of the Surgical Tool Unit

Figure 41:
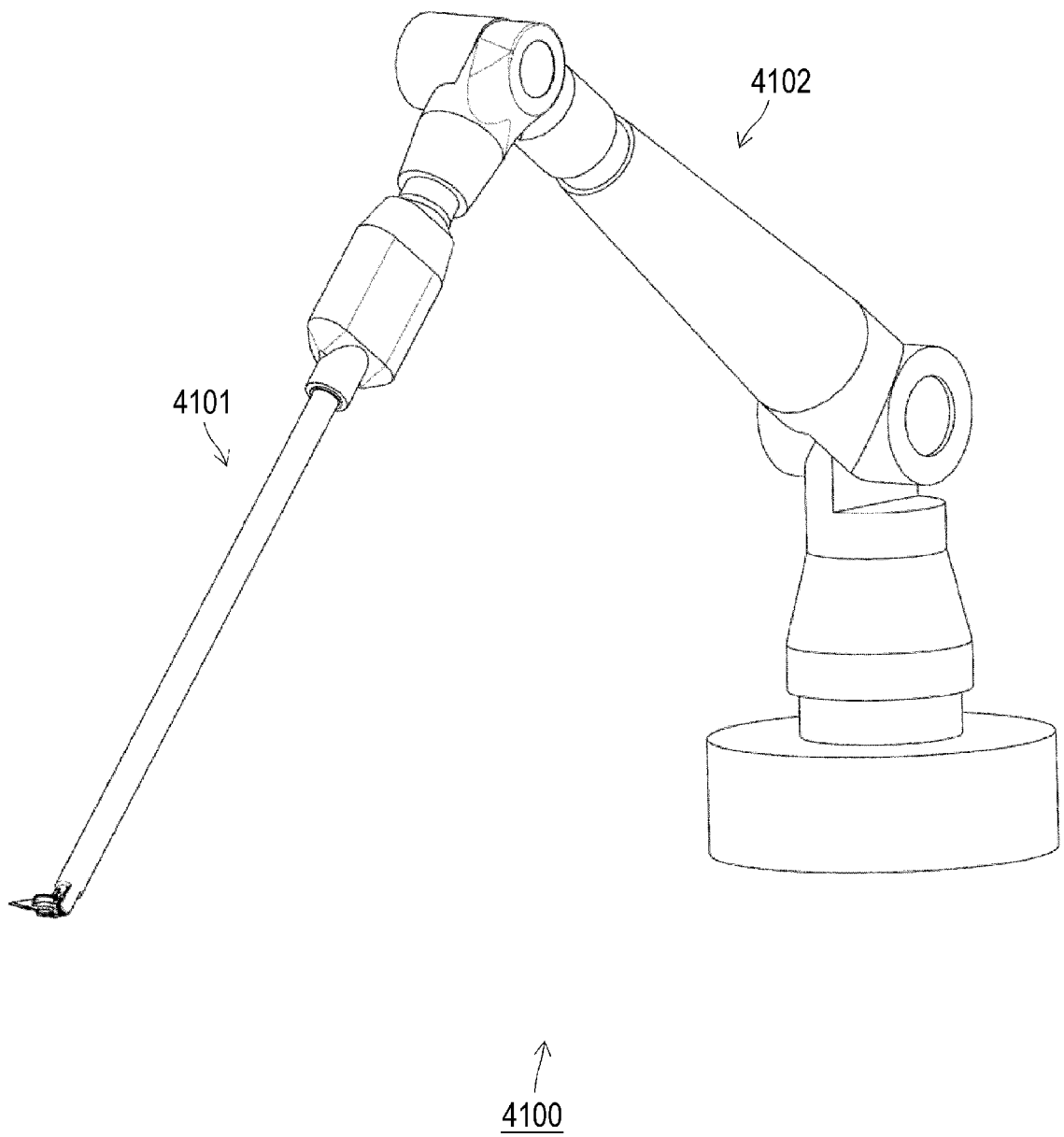
FIG. 41 is a diagram showing an example external configuration of a surgery support system 4100.

F-1. Example application to a computer-aided surgery system FIG. 41 shows an example external configuration of a surgery support system 4100 (also referred to as a computer-aided surgery system or a robotically-assisted surgery system) using a surgical tool unit according to this embodiment. The surgery support system 4100 shown in the drawing includes an arm 4101 having a multi-link structure, and a surgical tool unit 4102 is attached to the end of the arm 4101. The surgical tool unit 4102 may be replaceable. The surgery support system 4100 is used in laparoscopic surgery, for example, and the surgical tool unit end portion 101 is inserted into an abdominal cavity through a trocar (not shown), to perform an operation such as gripping and cutting of an affected part.

The surgery support system 4100 shown in the drawing may be used as the slave device in a master-slave robot, for example, and the arm 4101 and the surgical tool unit 4102 are driven in accordance with an instruction from the master device (not shown). Further, a bilateral control method is applied to this type of master-slave robot, for example. Furthermore, the surgery support system 4100 can also function as a surgical-tool-equipped arm when handled directly by the operator.

Note that the arm 4101 may be a robot of any mechanism type such as a polar-coordinate robot, a cylindrical coordinate robot, a Cartesian coordinate robot, a vertical articulated robot, a horizontal articulated robot, a parallel link robot, or a remote center of motion (RCM) robot.

Further, in a case where the surgery support system 4100 is a surgical robot that supports laparoscopic surgery, the arm 4101 is preferably a vertical articulated arm or a remote center of motion (RCM) arm that has its remote rotation center at a position away from the driving rotation center and performs a pivoting (fixed-point) motion, so as to achieve compactness of the mechanism, ease of a pivoting motion generation at the site of a trocar, and the like.

Furthermore, although FIG. 41 shows an example configuration of a computer-aided surgery system to which only one surgical tool unit can be attached, the present technology can also be applied to a computer-aided surgery system of a type to which a plurality of surgical tool units can be simultaneously attached to perform laparoscopic surgery.

F-2. Example Application to a Surgical Operating Unit

FIG. 42 shows an example external configuration of a surgical operating unit 4200 using a surgical tool unit according to this embodiment. The surgical operating unit 4200 includes a handle unit 4201 that is directly held and operated by a user (operator) by hand, and a surgical tool unit 4202 is attached to the end of the handle unit 4201. The surgical tool unit 4202 may be replaceable.

The handle unit 4201 may include a joystick 4203 that can be handled with a thumb to designate a desired orientation of the posture of the surgical tool unit end portion of the surgical tool unit 4202, for example. The handle unit 4201 may also include a button 4204 that can be pushed with an index finger to issue an instruction for an opening and closing operation of the jaw members.

A controller (not shown) is installed in the handle unit 4201. The controller calculates the turning angle of the wrist element WE about the first axis, and the turning angle and the open angle of the end effector about the second axis, in accordance with the amount of operation of the joystick 4203 or the button 4204. The controller then converts these angles into the amount of rotation of each motor, and outputs a control signal to the surgical tool unit drive unit 103.

G. Effects

By the technology according to the present disclosure, operations with three degrees of freedom, which are a yaw operation, a pitch operation, and an opening and closing operation of the end effector at the end of a surgical tool, can be performed with three motors. Thus, the drive unit of the surgical tool can be made smaller in size.

Also, by the technology according to the present disclosure, a yaw operation, a pitch operation, and an opening and closing operation of the end effector at the end of a surgical tool can be performed with a structure that does not cause cross-axis interference. Thus, control on each axis becomes much easier.

INDUSTRIAL APPLICABILITY

The technology according to the present disclosure has been described in detail so far, with reference to specific embodiments. However, it is obvious that those skilled in the art can make modifications to and substitutions of the embodiments without departing from the scope of the technology according to the present disclosure.

In this specification, embodiments in which the technology according to the present disclosure is applied to a surgical tool to be used in a surgical robot have been mainly described. However, the subject matter of the technology according to the present disclosure is not limited to these embodiments. The technology according to the present disclosure can be applied to robots in various fields other than medical care, such as precision work robots. The technology according to the present disclosure can also be applied to a grip-type operating unit and a precision work device a user can operate while gripping it with a hand.

In short, the technology according to the present disclosure has been described through examples, and the descriptions in this specification should not be interpreted in a restrictive manner. The claims should be taken into account in understanding the subject matter of the technology according to the present disclosure.

Note that the technology according to the present disclosure may also be embodied in the configurations described below.

(1) A surgical tool including:
- a shaft;
- a wrist that is connected to an end of the shaft and is rotatable about a first axis;
- a first jaw member and a second jaw member that are supported rotatably about a second axis with respect to the wrist;
- a set of first forward and backward cables that transmits a force for turning the first jaw member about the second axis;
- a set of second forward and backward cables that transmits a force for turning the second jaw member about the second axis; and
- a turning motion unit that generates a turning motion of the wrist about the first axis so that pre-tension of the set of first forward and backward cables and the set of second forward and backward cables does not change.

(2) The surgical tool according to (1), further including:

a first jaw capstan that is provided on the first jaw member and has a rotation axis that is the second axis, the set of first forward and backward cables being wound around the first jaw capstan; and a second jaw capstan that is provided on the second jaw member and has a rotation axis that is the second axis, the set of second forward and backward cables being wound around the second jaw capstan.

(3) The surgical tool according to (2), further including:

a first idler pulley unit that switches the set of first forward and backward cables to a direction substantially parallel to a longitudinal axis of the shaft; and a second idler pulley unit that switches the set of second forward and backward cables to a direction substantially parallel to the longitudinal axis of the shaft.

(4) The surgical tool according to (3), in which the first idler pulley unit includes a first idler pulley that rotates about the first axis, and a first adjacent idler pulley that is adjacent to the first idler pulley and has a rotation axis parallel to the first axis, and the second idler pulley unit includes a second idler pulley that rotates about the first axis, and a second adjacent idler pulley that is adjacent to the second idler pulley and has a rotation axis parallel to the first axis.

(5) The surgical tool according to (3) or (4), further including:

a first actuator that rotates a first drive capstan and pulls the set of first forward and backward cables; and a second actuator that rotates a second drive capstan and pulls the set of second forward and backward cables.

(6) The surgical tool according to (5), in which the turning motion unit generates a turning motion of the wrist about the first axis by causing one of the set of first forward and backward cables and the set of second forward and backward cables to move backward and the other one to move forward in a longitudinal axis direction of the shaft.

(7) The surgical tool according to (6), in which the turning motion unit includes:

a first slide base that secures the first actuator and the first drive capstan, and slides in the longitudinal axis direction of the shaft;

a second slide base that secures the second actuator and the second drive capstan, and slides in the longitudinal axis direction of the shaft; and a forward and backward motion unit that causes the first slide base and the second slide base to move forward and backward in the longitudinal axis direction of the shaft, and generates a turning motion of the wrist about the first axis, on the basis of forward and backward motions of the first slide base and the second slide base.

(8) The surgical tool according to (6), in which the first actuator and the first drive capstan, and the second actuator and the second drive capstan are secured to the shaft, and the turning motion unit includes:

a first slide base that secures an idler pulley through which the set of first forward and backward cables is wound around the first drive capstan, and slides in the longitudinal axis direction of the shaft;

a second slide base that secures an idler pulley through which the set of second forward and backward cables is wound around the second drive capstan, and slides in the longitudinal axis direction of the shaft; and a forward and backward motion unit that causes the first slide base and the second slide base to move forward and backward in the longitudinal axis direction of the shaft, and generates a turning motion of the wrist about the first axis, in accordance with forward and backward motions of the first slide base and the second slide base.

(9) The surgical tool according to (7) or (8), in which the forward and backward motion unit includes:

a third actuator that rotates a third drive capstan; and a set of third forward and backward cables that is wound around the third drive capstan, the respective ends of the set of third forward and backward cables being secured to the first slide base and the second slide base, and generates forward and backward motions of the first slide base and the second slide base from rotation of the third drive capstan.

(10) The surgical tool according to (5), in which the first actuator and the first drive capstan, and the second actuator and the second drive capstan are secured to the shaft, and the turning motion unit includes: a wrist capstan that is provided on the wrist and has a rotation axis that is the first axis, the set of third forward and backward cables being wound around the wrist capstan; a third actuator that rotates a third drive capstan and pulls the third cable set; and an adjustment unit that adjusts pre-tension of the set of first forward and backward cables and the set of second forward and backward cables, in accordance with a turning motion of the wrist about the first axis.

(11) The surgical tool according to (10), in which the adjustment unit includes:

a first slide base that secures an idler pulley through which the set of first forward and backward cables is wound around the first drive capstan, and slides in a longitudinal axis direction of the shaft; and a second slide base that secures an idler pulley through which the set of second forward and backward cables is around the second drive capstan, and slides in the longitudinal axis direction of the shaft, and adjusts the pre-tension of the set of first forward and backward cables and the set of second forward and backward cables, by causing the first slide base and the second slide base to move forward and backward in accordance with a turning motion of the wrist about the first axis.

(12) The surgical tool according to (11), in which the adjustment unit further includes:

a fourth idler pulley that is secured to the shaft; and a set of fourth forward and backward cables that is wound around the fourth idler pulley, the respective ends of the set of fourth forward and backward cables being secured to the first slide base and the second slide base, and adjusts the pre-tension force of the set of first forward and backward cables and the set of second forward and backward cables, by causing the first slide base and the second slide base to move forward and backward in accordance with a turning motion of the wrist about the first axis, using a tractive force of the set of fourth forward and backward cables.

(13) A surgery support system including a surgical tool, and an arm to which the surgical tool is attached, the surgical tool including:

a shaft;

a wrist that is connected to an end of the shaft and is rotatable about a first axis;

a first jaw member and a second jaw member that are supported rotatably about a second axis with respect to the wrist;
a set of first forward and backward cables that transmits a force for turning the first jaw member about the second axis;
a set of second forward and backward cables that transmits a force for turning the second jaw member about the second axis; and
a turning motion unit that generates a turning motion of the wrist about the first axis so that pre-tension of the set of first forward and backward cables and the set of second forward and backward cables does not change.

(14) A surgical operating unit including a surgical tool, and a handle unit to which the surgical tool is attached, the surgical tool including:
a shaft;
a wrist that is connected to an end of the shaft and is rotatable about a first axis;
a first jaw member and a second jaw member that are supported rotatably about a second axis with respect to the wrist;
a set of first forward and backward cables that transmits a force for turning the first jaw member about the second axis;
a set of second forward and backward cables that transmits a force for turning the second jaw member about the second axis; and
a turning motion unit that generates a turning motion of the wrist about the first axis so that pre-tension of the set of first forward and backward cables and the set of second forward and backward cables does not change.

REFERENCE SIGNS LIST

100 Surgical tool unit
101 Surgical tool unit end portion
102 Shaft
103 Surgical tool unit drive unit
2300 Surgical tool unit
2301 Surgical tool unit end portion
2302 Shaft
2303 Surgical tool unit drive unit
3100 Surgical tool unit
3101 Surgical tool unit end portion
3102 Shaft
3103 Surgical tool unit drive unit
4100 Computer-aided surgery system
4101 Arm
4102 Surgical tool unit
4200 Surgical operating unit
4201 Handle unit
4202 Surgical tool unit
4203 Joystick
4204 Button

The invention claimed is:
1. A surgical tool, comprising:
a shaft;
a wrist connected to an end of the shaft, wherein the wrist is rotatable about a first axis;
a first jaw member;
a second jaw member, wherein each of the first jaw member and the second jaw member is rotatable about a second axis with respect to the wrist;
a set of first forward and backward cables configured to transmit a first force to turn the first jaw member about the second axis;
a set of second forward and backward cables configured to
transmit a second force to turn the second jaw member about the second axis;
a set of third forward and backward cables;
a first drive capstan;
a second drive capstan;
a third drive capstan;
a first actuator configured to:
rotate the first drive capstan; and
pull the set of first forward and backward cables;
a second actuator configured to:
rotate the second drive capstan; and
pull the set of second forward and backward cables, wherein each of the first actuator, the first drive capstan, the second actuator, and the second drive capstan is secured to the shaft;
a third actuator configured to:
rotate the third drive capstan;
pull the set of third forward and backward cables;
generate a turning motion of the wrist about the first axis; and
adjust, based on the generated turning motion of the wrist about the first axis, a pre-tension of the set of first forward and backward cables and a pre-tension of the set of second forward and backward cables, wherein the pre-tension of the set of first forward and backward cables and the pre-tension of the set of second forward and backward cables does not change based on the adjustment;
a wrist capstan on the wrist, wherein
the wrist capstan has a first rotation axis that is the first axis, and
the set of third forward and backward cables is wound around the wrist capstan;
a first jaw capstan on the first jaw member, wherein
the first jaw capstan has a second rotation axis that is the second axis, and
the set of first forward and backward cables is wound around the first jaw capstan;
a second jaw capstan on the second jaw member, wherein
the second jaw capstan has a third rotation axis that is the second axis, and
the set of second forward and backward cables is wound around the second jaw capstan;
a first idler pulley unit configured to switch the set of first forward and backward cables to a specific direction, wherein the specific direction is substantially parallel to a longitudinal axis of the shaft; and
a second idler pulley unit configured to switch the set of second forward and backward cables to the specific direction.

2. The surgical tool according to claim 1, wherein the first idler pulley unit includes:
a first idler pulley configured to rotate about the first axis, and
a first adjacent idler pulley adjacent to the first idler pulley, wherein
the first adjacent idler pulley has a fourth rotation axis parallel to the first axis, and
the second idler pulley unit includes:
a second idler pulley configured to rotate about the first axis, and
a second adjacent idler pulley adjacent to the second idler pulley, wherein the second adjacent idler pulley has a fifth rotation axis parallel to the first axis.

3. The surgical tool according to claim 1, wherein the third actuator is further configured to:
   cause one of the set of first forward and backward cables or the set of second forward and backward cables to move backward in a longitudinal axis direction of the shaft and other one of the set of first forward and backward cables or the set of second forward and backward cables to move forward in the longitudinal axis direction of the shaft; and
   generate the turning motion of the wrist about the first axis based on the one of the movement of the set of first forward and backward cables or the set of second forward and backward cables backward in the longitudinal axis direction of the shaft and the movement of the other one of one of the set of first forward and backward cables or the set of second forward and backward cables forward in the longitudinal axis direction of the shaft.

4. The surgical tool according to claim 3, further comprising:
   a first slide base configured to:
      secure the first actuator and the first drive capstan; and
      slide in the longitudinal axis direction of the shaft; and
   a second slide base configured to:
      secure the second actuator and the second drive capstan; and
      slide in the longitudinal axis direction of the shaft, wherein the third actuator and the set of third forward and backward cables are configured to:
         cause the first slide base and the second slide base to move forward and backward in the longitudinal axis direction of the shaft; and
         generate the turning motion of the wrist about the first axis, based on forward and backward motions of the first slide base and the second slide base.

5. The surgical tool according to claim 4, wherein
   each end of the set of third forward and backward cables being is secured to the first slide base and the second slide base, and
   the set of third forward and backward cables is configured to generate the forward and backward motions of the first slide base and the second slide base based on the rotation of the third drive capstan.

6. The surgical tool according to claim 3, wherein
   the first idler pulley unit includes a first idler pulley,
   the second idler pulley unit includes a second idler pulley, and
   the surgical tool further comprises:
      a first slide base configured to:
         secure the first idler pulley through which the set of first forward and backward cables is wound around the first drive capstan; and
         slide in the longitudinal axis direction of the shaft; and
      a second slide base configured to:
         secure the second idler pulley through which the set of second forward and backward cables is wound around the second drive capstan; and
         slide in the longitudinal axis direction of the shaft.

7. The surgical tool according to claim 1, wherein
   the first idler pulley unit includes a first idler pulley,
   the second idler pulley unit includes a second idler pulley,
   the surgical tool further comprises:
      a first slide base configured to:
         secure the first idler pulley through which the set of first forward and backward cables is wound around the first drive capstan; and
         slides slide in a longitudinal axis direction of the shaft; and
      a second slide base configured to:
         secure the second idler pulley through which the set of second forward and backward cables is around the second drive capstan; and
         slide in the longitudinal axis direction of the shaft, and
   the third actuator is further configured to:
      cause each of the first slide base and the second slide base to move forward and backward based on the generated turning motion of the wrist about the first axis; and
      adjust the pre-tension of the set of first forward and backward cables and the pre-tension of the set of second forward and backward cables based on forward and backward movements of each of the first slide base and the second slide base.

8. The surgical tool according to claim 7, further comprising:
   a third idler pulley secured to the shaft; and
   a set of fourth forward and backward cables, wherein
      the set of fourth forward and backward cables is wound around the third idler pulley, and
      each end of the set of fourth forward and backward cables is secured to the first slide base and the second slide base, and
      the third idler pulley and the set of fourth forward and backward cables are configured to:
         cause the first slide base and the second slide base to move forward and backward based on the turning motion of the wrist about the first axis, by use of a tractive force of the set of fourth forward and backward cables; and
         adjust each of the pre-tension of the set of first forward and backward cables and the pre-tension of the set of second forward and backward cables based on the forward and backward movements of the first slide base and the second slide base.

9. A surgery support system, comprising:
   a surgical tool; and
   an arm to which the surgical tool is attached, wherein the surgical tool includes
   a shaft;
   a wrist connected to an end of the shaft, wherein the wrist is rotatable about a first axis;
   a first jaw member;
   a second jaw member, wherein each of the first jaw member and the second jaw member is rotatable about a second axis with respect to the wrist;
   a set of first forward and backward cables configured to transmit a first force to turn the first jaw member about the second axis;
   a set of second forward and backward cables configured to
   transmit a second force to turn the second jaw member about the second axis;
   a set of third forward and backward cables;
   a first drive capstan;
   a second drive capstan;
   a third drive capstan;
   a first actuator configured to:
      rotate the first drive capstan; and
      pull the set of first forward and backward cables;
   a second actuator configured to:
      rotate the second drive capstan; and
      pull the set of second forward and backward cables, wherein each of the first actuator, the first drive capstan, the second actuator, and the second drive capstan is secured to the shaft;
a third actuator configured to:
  rotate the third drive capstan;
  pull the set of third forward and backward cables;
  generate a turning motion of the wrist about the first axis;
  adjust, based on the generated turning motion of the wrist about the first axis, a pre-tension of the set of first forward and backward cables and a pre-tension of the set of second forward and backward cables,
  wherein the pre-tension of the set of first forward and backward cables and the pre-tension of the set of second forward and backward cables does not change based on the adjustment;
a wrist capstan on the wrist, wherein
  the wrist capstan has a first rotation axis that is the first axis, and
  the set of third forward and backward cables is wound around the wrist capstan;
a first jaw capstan on the first jaw member, wherein
  the first jaw capstan has a second rotation axis that is the second axis, and
  the set of first forward and backward cables is wound around the first jaw capstan;
a second jaw capstan on the second jaw member, wherein
  the second jaw capstan has a third rotation axis that is the second axis, and
  the set of second forward and backward cables is wound around the second jaw capstan;
a first idler pulley unit configured to switch the set of first forward and backward cables to a specific direction wherein the specific direction is substantially parallel to a longitudinal axis of the shaft; and
a second idler pulley unit configured to switch the set of second forward and backward cables to the specific direction parallel to the longitudinal axis of the shaft.

10. A surgical operating unit, comprising:
a surgical tool; and
a handle unit to which the surgical tool is attached, wherein the surgical tool includes:
a shaft;
a wrist connected to an end of the shaft, wherein the wrist is rotatable about a first axis;
a first jaw member;
a second jaw member, wherein each of the first jaw member and the second jaw member is rotatable about a second axis with respect to the wrist;
a set of first forward and backward cables configured to transmit a first force to turn the first jaw member about the second axis;
a set of second forward and backward cables configured to transmit a second force to turn the second jaw member about the second axis;
a set of third forward and backward cables;
a first drive capstan;
a second drive capstan;
a third drive capstan;
a first actuator configured to:
  rotate the first drive capstan; and
  pull the set of first forward and backward cables;
a second actuator configured to:
  rotate the second drive capstan; and
  pull the set of second forward and backward cables,
  wherein each of the first actuator, the first drive capstan, the second actuator, and the second drive capstan is secured to the shaft;
a third actuator configured to:
  rotate the third drive capstan;
  pull the set of third forward and backward cables;
  generate a turning motion of the wrist about the first axis;
  adjust, based on the generated turning motion of the wrist about the first axis, a pre-tension of the set of first forward and backward cables and a pre-tension of the set of second forward and backward cables,
  wherein the pre-tension of the set of first forward and backward cables and the pre-tension of the set of second forward and backward cables does not change based on the adjustment;
a wrist capstan on the wrist, wherein
  the wrist capstan has a first rotation axis that is the first axis, and
  the set of third forward and backward cables is wound around the wrist capstan;
a first jaw capstan on the first jaw member, wherein
  the first jaw capstan has a second rotation axis that is the second axis, and
  the set of first forward and backward cables is wound around the first jaw capstan;
a second jaw capstan on the second jaw member, wherein
  the second jaw capstan has a third rotation axis that is the second axis, and
  the set of second forward and backward cables is wound around the second jaw capstan;
a first idler pulley unit configured to switch the set of first forward and backward cables to a specific direction wherein the specific direction is substantially is parallel to a longitudinal axis of the shaft; and
a second idler pulley unit configured to switch the set of second forward and backward cables to the specific direction.

* * * * *